United States Patent
Motoki et al.

(10) Patent No.: US 6,752,758 B2
(45) Date of Patent: Jun. 22, 2004

(54) ENDOSCOPE APPARATUS

(75) Inventors: Nobuyuki Motoki, Hachioji (JP);
Mitsunobu Ono, Tokyo (JP);
Takakazu Ishigami, Tama (JP);
Hiroyuki Fukuda, Hino (JP);
Yoshihiro Hayashi, Hachioji (JP);
Kenji Murakami, Yamato (JP);
Yasufumi Shimoe, Fukuyama (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 10/413,694

(22) Filed: Apr. 15, 2003

(65) Prior Publication Data

US 2003/0195389 A1 Oct. 16, 2003

Related U.S. Application Data

(63) Continuation of application No. 09/817,931, filed on Mar. 27, 2001, now Pat. No. 6,569,086.

(30) Foreign Application Priority Data

Mar. 27, 2000 (JP) ........................................ 2000-086993
Apr. 5, 2000 (JP) ........................................ 2000-103858

(51) Int. Cl.[7] ................................................ A61B 1/00
(52) U.S. Cl. ...................... 600/146; 600/104; 600/120; 600/143; 348/65
(58) Field of Search ................................. 600/104, 114, 600/115, 120–122, 143, 142, 146–148, 151, 152, 131, 119; 604/95.05; 348/65, 68, 69, 45

(56) References Cited

U.S. PATENT DOCUMENTS

| | | | |
|---|---|---|---|
| 4,499,895 A | * | 2/1985 | Takayama ................... 600/152 |
| 4,895,431 A | | 1/1990 | Tsujiuchi et al. |
| 5,007,406 A | | 4/1991 | Takahashi et al. |
| 5,159,446 A | | 10/1992 | Hibino et al. |
| 5,255,668 A | * | 10/1993 | Umeda ........................ 600/139 |
| 5,279,559 A | * | 1/1994 | Barr ......................... 604/95.05 |
| 5,373,317 A | | 12/1994 | Salvati et al. |
| 6,569,086 B2 | * | 5/2003 | Motoki et al. ............. 600/146 |

FOREIGN PATENT DOCUMENTS

EP     0 543 738 A1    5/1993
JP     10-328131       12/1998

* cited by examiner

Primary Examiner—Tu Ba Hoang
(74) Attorney, Agent, or Firm—Scully, Scott, Murphy & Presser

(57) ABSTRACT

An operational remote controller integrates a joystick for bending a bending portion of an inserted portion in an endoscope. A bending lever stands on the joystick. For every automatically returning of the bending lever to a neutral position, a CPU of the operational remote controller detects the neutral position and sets an insensitive band within a predetermined range of the neutral position. Thus, the insensitive band can be set within a relatively narrow range irrespective of variation of neutral positions. The CPU supplies positional information of the bending lever to a control circuit for controlling a motor drive circuit. The control circuit controls a motor drive circuit based on the supplied positional information, and the motor drive circuit drives a motor to bend the bending portion of the inserted portion.

19 Claims, 15 Drawing Sheets

ENDOSCOPE APPARATUS

This application claims benefit of Japanese Applications No. 2000-086993 filed in Japan on Mar. 27, 2000, No. 2000-103858 filed in Japan on Apr. 5, 2000, the contents of which are incorporated by this reference.

BACKGROUND OF THE INVENTION

1. Field of the Invention

The present invention relates to an endoscope apparatus suitable to bend a bending portion provided for a tip of an inserted portion of an endoscope by using a joystick.

2. Prior Art Statement

Conventionally, an endoscope apparatus has been widely used. The endoscope apparatus observes an examined site and performs various processings by inserting a long inserted portion into a body cavity. Also, in an industrial field, an (industrial) endoscope apparatus has been widely used. The (industrial) endoscope apparatus can observe and inspect an internal defect, corrosion, etc. of a boiler, turbine, engine, chemical plant, and the like.

The above-mentioned endoscope apparatus is structured such that a bending portion capable of being manually operated is provided at a base-end side of a tip of the long inserted portion. The inserted portion has a CCD, etc. which is an image pickup means at the tip and a camera control unit (hereinafter, referred to as a CCU) at the side near hand.

Image information obtained by using the CCD is transmitted to the CCU so that a video signal is generated. An endoscope image can be displayed by supplying the video signal to a display apparatus such as an LCD, a CRT, or the like.

Bending operation of the bending portion can be remotely operated by an operational remote controller for endoscope (hereinafter, referred to as an operational remote controller). That is, the endoscope apparatus has therein a motor for bending which can be controlled by the operational remote controller. In the endoscope apparatus, a wire placed at the bending portion is towed and loosened by using a power of the motor, thereby enabling the bending portion to be remotely bent.

As the endoscope apparatus having the operational remote controller, an endoscope apparatus in which a joystick is provided as the operational remote controller for bending operation is proposed as disclosed in Japanese Laid-open Patent Publication No. 10-328131. Incidentally, a detailed operating method of the joystick in the endoscope apparatus is not disclosed in Japanese Laid-open Patent Publication No. 10-328131.

Also, for example, in an endoscope of European Patent Application Publication No. 0543738A1, an endoscope apparatus in which an electrically-driven bent inserted portion detachable from a processor control module is operated by a joystick is proposed. This reference discloses that, in the above-mentioned endoscope apparatus, the electrically-driven bent inserted portion is positionally controlled by the joystick. Further, the reference discloses that, in the above-mentioned endoscope apparatus, a bent shape is electrically perked (locked against bending). Incidentally, European Patent Application Publication No. 0543738A1 does not disclose a detailed operating method of an operational button, etc. for positional control and locking against bending in the endoscope apparatus.

The joysticks have variable resistors in which resistances are varied depending on inclination angles of a lever. The joysticks can output an analog voltage value in accordance with the inclination angles of the lever. As disclosed in European Patent Application Publication No. 0543738A1, the joystick is frequently used for the positional control.

As the positional control using the above-described joystick, a method for proportioning the inclination angle of the lever to an offset of a controlled target can be considered. For example, the positional control using the joystick has an advantage that an operator can easily grasp an actual angle of bending by proportioning the inclination angle of the lever (bending lever) to an inclination angle of the tip of the inserted portion.

However, when bending with an only fine angle, in the positional control using the joystick, the operational angle of the bending lever also must become fine. Thus, the operator needs to concentrate his attention to his fingertip and, therefore, fatigue from the operation is increased.

Then, in the endoscope-apparatus, a method (bending control at a constant speed) in which an output of the joystick is handled as a signal indicating only a direction, not as an analog value corresponding to the inclination angle of the level, and the bending portion is bent in a pushed-down direction of the lever at a constant speed; is put into practical use in order to solve the disadvantage of the positional control. Further, the endoscope apparatus, is sometimes employed, having a function switching the positional control and the bending control at the constant speed.

In the case of the bending control at the constant speed, the operator cannot arbitrarily change a bending speed. Therefore, in the endoscope apparatus using the bending control at the constant speed, the constant speed is set to a slow speed, that is, driving in a slow mode is frequent. When using the slow mode as the bending control at the constant speed, the operability at the time of fine adjustment of the bending angle is excellent, however, the above endoscope apparatus has a problem that it takes a long time until the inclination angle reaches a desired bending angle. In contrast, when using a fast speed as the bending control at the constant speed, the above endoscope apparatus has a problem that the operability at the time of fine adjustment is remarkably reduced.

In the endoscope apparatus disclosed in European Patent Application Publication No. 0543738A1, the bending locking of the bending portion is on by operating a bending lock switch which is laid out at a position different from that of the joystick for bending operation. Therefore, in the endoscope apparatus, the bending locking cannot be performed by one-hand operation.

In the endoscope apparatuses, generally, it is impossible to confirm whether or not the bending portion is locked and, therefore, it is confirmed by employing light on/off of an LED, etc. near a switch. However, the operator must look aside from a monitor on which an endoscope image, etc. is displayed to confirm whether or not the bending portion is locked by employing light on/off of the LED, etc., thereby the operability is inferior.

When the lever is not operated, the joystick is automatically returned near a neutral position by energizing power of a spring. However, there is a problem that the neutral position of the automatic returned lever is largely varied depending on precision of a spring or mechanism of the joystick.

In the inventor's opinion, the periphery of the neutral position is set to an insensitive band taking account of the variation. When the lever is located at the neutral position, a method for stopping an output of a positional information signal can be considered.

However, the above-mentioned method has a problem that the lever operation is not available within a predetermined range near the neutral position and the bending operation is possible only by relatively largely inclining the lever.

On the other hand, in a conventional endoscope apparatus for always transmitting positional information without setting the insensitive band, even if the lever is not operated, the positional information of the lever is outputted from the joystick. Therefore, the conventional endoscope apparatus has a problem that processing efficiency of a CPU is reduced when using a controller for controlling by using the positional information of the lever from the joystick.

For the above reasons, in the endoscope apparatuses, the precision of operability of the joystick cannot be increased.

Operational remote controllers with the above-mentioned joysticks having a display for supplying a video signal which is signal-processed by the CCU to display the signal as an observed image are proposed as disclosed in, for example, Japanese Laid-open Patent Publication No. 10-328131 and U.S. Pat. No. 5,373,317.

The operational remote controller disclosed in Japanese Laid-open Patent Publication No. 10-328131 is structured such that a display and a joystick is provided for a case having a predetermined volume. Since the above operational remote controller has only the joystick for bending operation, it has a problem that operations other than the bending control cannot be executed.

In contrast, the operational remote controller disclosed in U.S. Pat. No. 5,373,317 is provided-with a display, a joystick, and key switches for various operations. The motor, and a signal processing control unit for processing an image pickup signal from image pickup means are provided in a case.

Since the above operational remote controller has the motor, signal processing control unit, and display, there is a problem that the outer shape of the case is large, the weight is heavy, and various operations are impossible while supporting the above operational remote controller by one-handed grasping. Further, since the key switches are adjacent to the display in the above operational remote controller, there is also a problem that it is not user-friendly because the key switches are operated only by positioning the hand aside from the joystick or only by operation using the hand which grasps an inserted portion.

OBJECTS AND SUMMARY OF THE INVENTION

It is one object of the present invention to provide an endoscope apparatus capable of improving bending operability using a joystick.

It is another object of the present invention to provide an endoscope apparatus capable of improving the operational precision of bending using the joystick.

It is further another object of the present invention to provide an endoscope apparatus capable of user-friendlily performing operation necessary for observation and inspection by one hand while performing bending operation with small size and light weight.

According to the present invention, an endoscope apparatus includes: bending drive means for bending a bending portion provided to a tip of an inserted portion; an operating unit for bending and operating the bending portion by inclining a lever; and control means for allowing the bending drive means to bend and operate the bending portion based on information from the operating unit, for detecting the neutral position for every automatically returning of the lever to the neutral position, and for setting a predetermined range from the detected neutral position to an insensitive band to prohibit bending driving of the bending portion by the bending drive means.

According to the present invention, an endoscope apparatus includes: bending drive means for bending a bending portion provided for a tip of an inserted portion; a bending operating unit for bending the bending portion by inclining a lever; and a plurality of operating units, which are provided for remotely controlling the endoscope apparatus, other than said bending operating unit and are provided distributively on the front surface and a back surface of a case of an operational remote controller for endoscope.

The above and many other objects, features, and advantages of this invention will become apparent from the ensuing detailed description of one preferred embodiment, which should be read in conjunction with the accompanying drawing.

DETAILED DESCRIPTION OF THE PREFERRED EMBODIMENT

Figure 1:
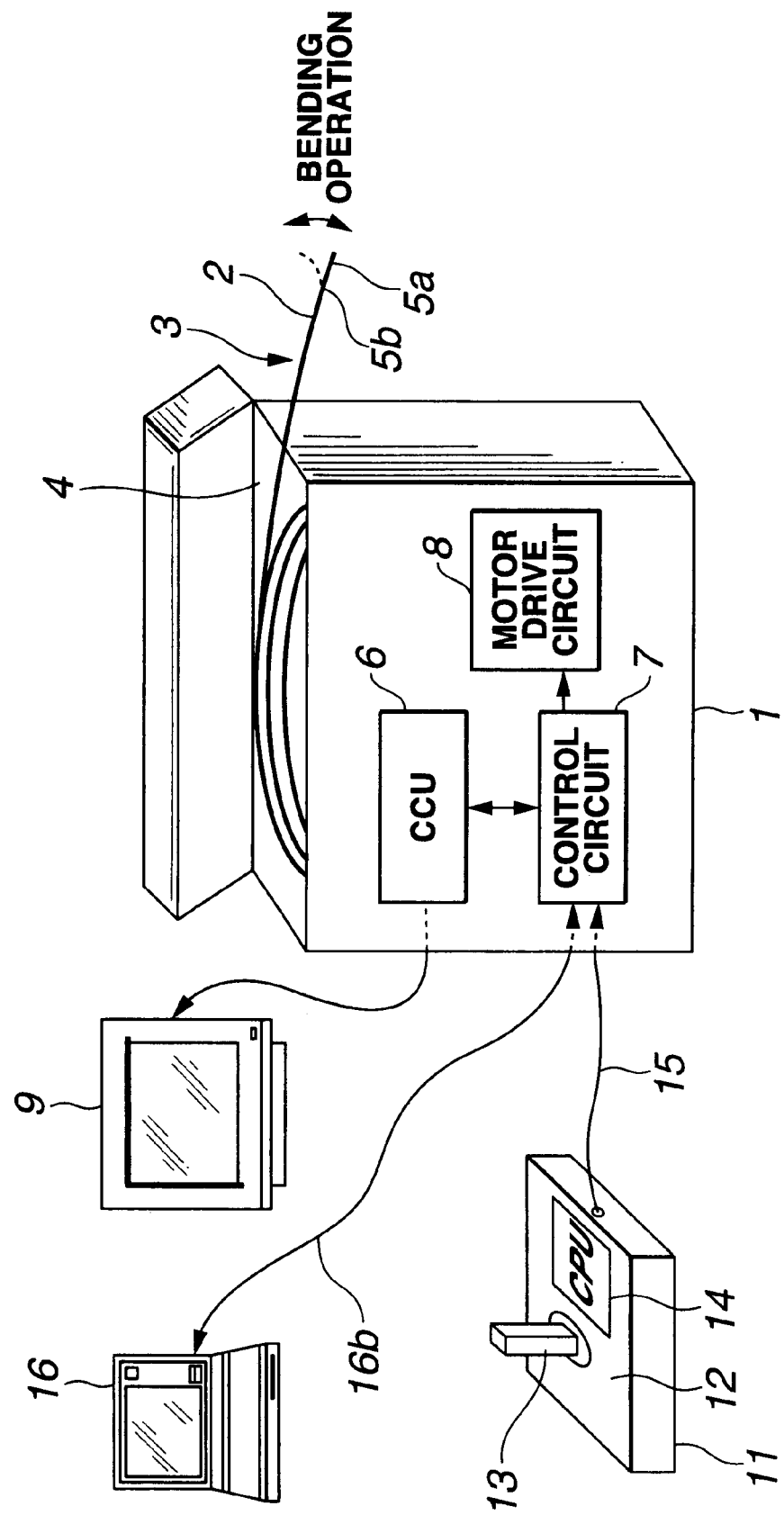
FIG. 1 is an explanatory view of the overall endoscope system including an endoscope apparatus according to a first embodiment of the present invention.
Figure 2:
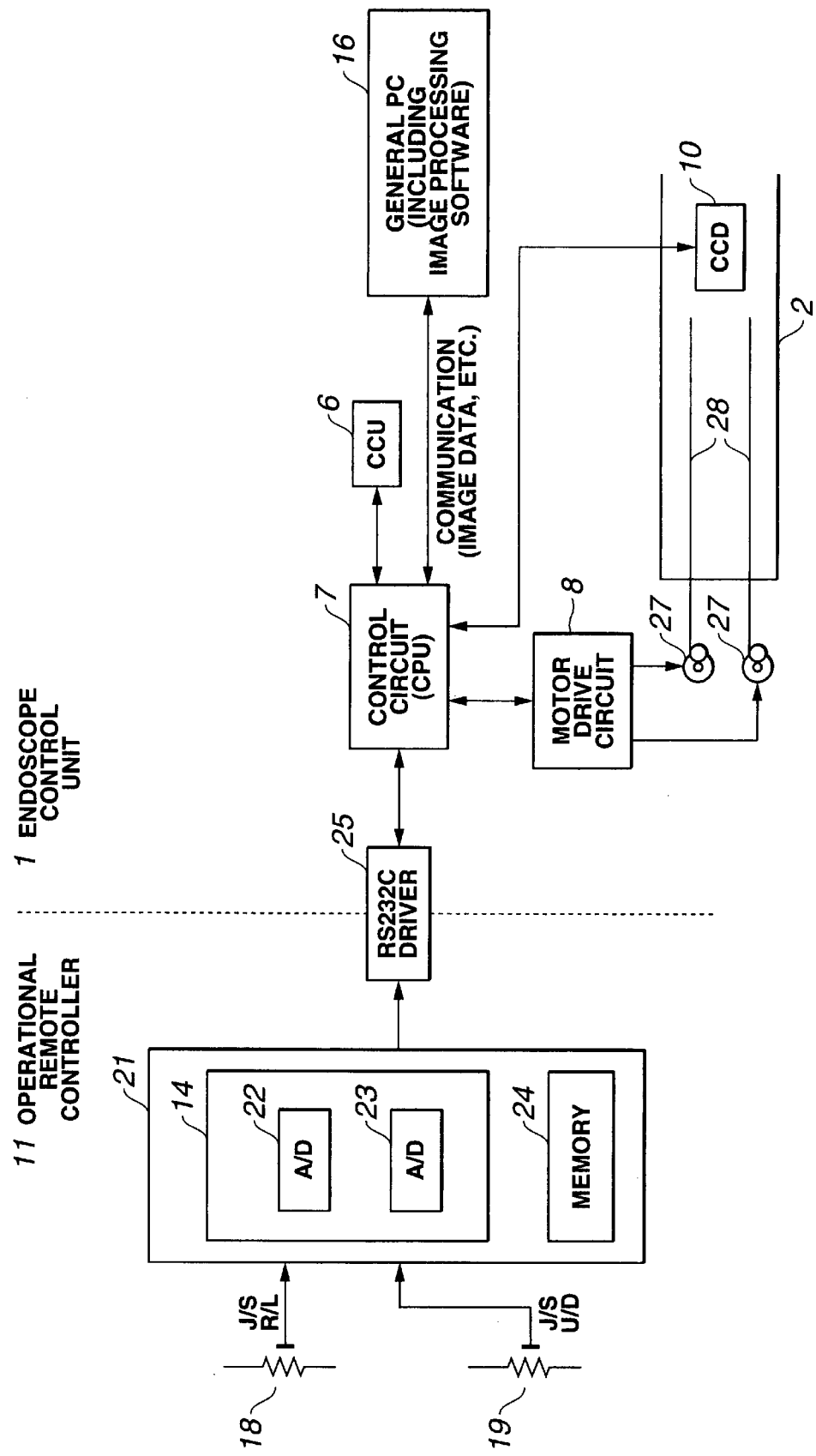
FIG. 2 is a block diagram showing the constitution of circuits in the endoscope apparatus.
Figure 3:
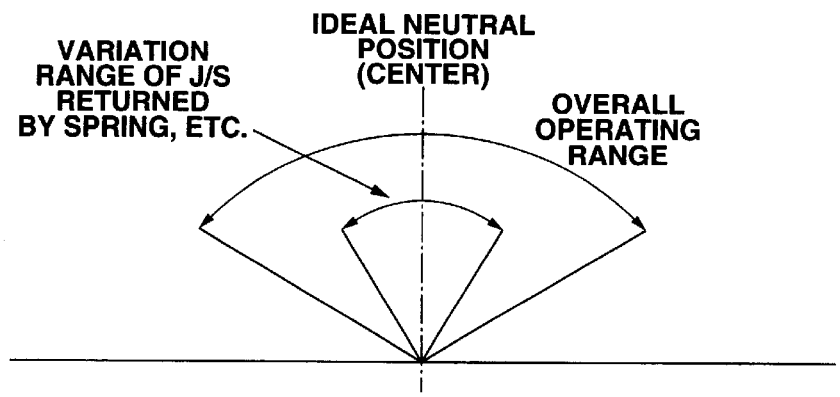
FIG. 3 is an explanatory view for explaining an operating range of a joystick.
Figure 4:
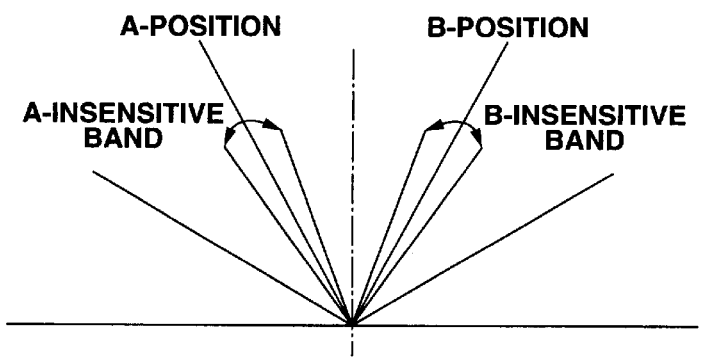
FIG. 4 is an explanatory view for explaining operation according to the first embodiment.

FIGS. 1 to 4 relate to first to fourth embodiments of the present invention in which FIG. 1 is an explanatory view showing the overall of an endoscope system including an endoscope apparatus according to the first embodiment; FIG. 2 is a block diagram showing the constitution of circuits in the endoscope apparatus; FIG. 3 is an explanatory view for explaining an operating range of a joystick; and FIG. 4 is an explanatory view for operation according to the first embodiment.

In the present embodiment, operational precision is improved by narrowing an insensitive range of a neutral position where an angle signal from a joystick should be stopped.

An endoscope control unit 1 includes an accommodating unit 4 for accommodating an endoscope 3 having a long inserted portion 2. The inserted portion 2 of the endoscope 3 has a bending portion 5b provided at a base-end side of a hard end portion 5a and is bendable. The endoscope control unit 1 comprises a CCU 6; a control circuit 7; and a motor drive circuit 8. The control circuit 7 controls each section of the endoscope control unit 1.

A CCD 10 (refer to FIG. 2) is provided for the end portion 5a of the endoscope 3. The CCD 10 photoelectrically converts an optical image of an object to be photographed, and outputs the converted signal to the camera control unit (hereinafter, referred to as the CCU) 6. The CCU 6 is controlled by the control circuit 7, thereby converting an input signal into a standard video signal for displaying it on a monitor.

The video signal from the CCU 16 is supplied to a monitor 9 via a cable. The monitor 9 displays an endoscope image onto a displayed screen based on the input video signal.

A general PC 16 and the control circuit 7 are connected via a predetermined interface cable 16b such as an RS232C or a USB. The general PC 16 incoporates image processing software. The endoscope control unit 1 can perform predetermined image processing for the endoscope image displayed on the monitor 9 via the control circuit 7 by operating the general PC 16.

As shown in FIG. 2, a plurality of wires for traction 28 are placed to the inserted portion 2. One end of each wire for traction 28 is fixed at a predetermined position of the inserted portion 2. In the endoscope 3, each wire for traction 28 is properly towed, thereby bending the bending portion 5b of the inserted portion 2. Each wire for traction 28 is towed by a plurality of motors 27. Each motor 27 is driven by a motor drive circuit 8, thereby towing the wires for traction 28. The motor drive circuit 8 is controlled by the control circuit 7, thereby controlling the driving of the motors 27.

In the present embodiment, an operational remote controller for endoscope (hereinafter, referred to as an operational remote controller) 11 integrating a joystick 12 is used as remote control means for bending operation. A bending lever 13 of the joystick 12 capable of being inclined vertically and horizontally by operator's operation stands on an upper surface of the operational remote controller 11. When the operator performs no operation through the lever, the bending lever 13 is automatically returned near a predetermined neutral position by an energizing force of a spring (not shown).

As shown in FIG. 2, the joystick 12 has: a variable resistor 18 in which a resistance changes corresponding to inclination in a horizontal direction of the bending lever 13; and a variable resistor 19 in which a resistance changes corresponding to inclination in a vertical direction of the bending lever 13. The variable resistor 18 outputs a J/SR/L signal having a level corresponding to an inclination angle in the horizontal direction of the bending lever 13. The variable resistor 19 outputs a J/SU/D signal having a level corresponding to an inclination angle in the vertical direction of the bending lever 13.

Outputs from the variable resistors 18 and 19 are supplied to a CPU 14 of a remote control circuit 21 incorporated in the operational remote controller 11. The CPU 14 comprises A/D converters (A/Ds) 22 and 23. The A/Ds 22 and 23 convert the J/SR/L signal and the J/SU/D signal into digital signals and the CPU 14 fetches the converted signals.

The CPU 14 outputs the fetched J/SR/L signal and J/SU/D signal as positional information. In the example shown in FIG. 1, the operational remote controller 11 and control circuit 7 are connected by a remote controller cable 15 compliant with an RS232C standard, etc. The remote control circuit 21 outputs the positional information to the control circuit 7 via an RS232C driver 25.

In the present embodiment, the CPU 14 determines whether or not the bending lever 13 automatically returns to the neutral position by monitoring the J/SR/L signal and J/SU/D signal. When the CPU 14 determines that the bending lever 13 returns to the neutral position, the J/SR/L signal and J/SU/D signal in this case are stored in a memory 24 as the positional information at the neutral position.

Further, the CPU 14 sets an insensitive band within a predetermined range from the neutral position, as center, stored in the memory 24. If the CPU 14 determines based on the J/SR/L signal and J/SU/D signal that the inclination of the bending lever 13 is within the range of the insensitive band, transmission of the positional information to the control circuit 7 is stopped.

The positional information is supplied via the remote controller cable 15 and, based on the supplied positional information, the control circuit 7 controls the motor drive circuit 8, thereby bending the bending portion 5b with a bending angle based on the positional information.

Next, operation according to the embodiment with the above constitution will be described referring to FIGS. 3 and 4.

Assume that the operator bends the bending portion 5b of the endoscope inserted portion 2. The operator bends the bending portion 5b by using the bending lever 13 standing onto the operational remote controller 11. More specifically, the operator inclines the bending lever 13 in a direction corresponding to a direction in which the bending portion 5b is to be bent and inclines this inclination angle in accordance with the angle of bending.

The resistances of the variable resistors 18 and 19 in the joystick 12 change by the inclining operation of the bending lever 13, and the J/SR/L signal and J/SU/D signal with a level corresponding to the inclination angle are supplied to the CPU 14 of the remote control circuit 21. The CPU 14 fetches these signals by using the A/Ds 22 and 23 and outputs them as the positional information.

The positional information from the remote control circuit 21 is supplied to the control circuit 7 in the endoscope control unit 1 via the remote controller cable 15. The control circuit 7 controls the motor drive circuit 8 based on the positional information. Thus, the motor drive circuit 8 drives the motor 27 based on the positional information, thereby properly towing the wires 28 for traction. As a consequence, the bending portion 5b of the inserted portion 2 is bent in a direction and with an angle corresponding to the positional information.

Herein, assume that the operator does not touch the bending lever 13 of the joystick 12. Then, the inclination angle formed by the bending lever 13 of the joystick 12 changes to the periphery of the neutral position shown in FIG. 3 by an energizing force of a spring (not shown). In this case, the bending lever 13 is automatically returned to any position within varied range corresponding to the variation of the spring, etc. Incidentally, as shown in FIG. 3, an ideal neutral position of the bending lever 13 is the center within the overall operation (range of a maximum inclination angle formed by the bending lever 13) and the automatically-returned position is within a range of a predetermined variation around the neutral position.

When it is detected based on the output of the joystick 12 that the bending lever 13 returns to the automatically-returned position, the CPU 14 stores the positional information in this case in the memory 24. The CPU 14 sets an insensitive band within a predetermined range around the stored positional information. The CPU 14 determines whether or not voltages of the variable resistors 18 and 19 change for several seconds, thereby detecting whether or not the bending lever 13 returns to the automatically-returned position.

In the present invention, the returned positional information is stored in the remote control circuit 21 every automatic return and the insensitive band is set within a predetermined range from the stored position as center. For example, if the returned position is an A-position in FIG. 4, the CPU 14 sets an A-insensitive band shown by a curved arrow with the A-position as center. Also, for example, if the returned position is a B-position in FIG. 4, the CPU 14 sets a B-insensitive band shown by a curved arrow with the B-position as center.

The CPU 14 determines whether or not the inclination of the bending lever 13 is within the insensitive range based on the returned position stored in the memory 24 by monitoring the J/SR/L signal and J/SU/D signal from the joystick 12. If it is determined that the inclination of the bending lever 13 is within the insensitive range, the CPU 14 stops the transmission of the positional information to the control circuit 7.

Now assume that the operator does not touch the bending lever 13 after the bending lever 13 is automatically returned. In this case, the inclination of the bending lever 13 is within the range of the insensitive band. Therefore, no positional information is transmitted to the control circuit 7 from the remote control circuit 21. Since the control circuit 7 does not receive the positional information, the control operation is not performed in the control circuit 7 based on the positional information.

Herein, assume that the operator operates the bending lever 13 to bend the bending portion 5b. In this case, the operator inclines the bending lever 13 to exceed the set insensitive band. Then, the CPU 14 detects based on the received J/SR/L signal and the J/SU/D signal that the bending lever 13 inclines out of the range of the insensitive band, and the CPU 14 restarts the transmission of the positional information based on the J/SR/L signal and the J/SU/D signal. In this case, differently from the conventional art, the CPU 14 does not set the wide insensitive band which takes the variation of the spring, etc. into account. Therefore, the operator can instruct the bending by the operation through the lever with a relatively small inclination angle.

As a consequence, the control circuit 7 restarts receiving the positional information and restarts the controlling an operation based on the positional information obtained by the control of the motor drive circuit 8, etc.

As mentioned above, in the present embodiment, when the operator does not operate the bending lever 13 of the joystick 12, the control circuit 7 does not need to control with the bending operation. Therefore, the control circuit 7 can execute other processes such as communication with the general PC 16 and image processing during a time for processing the positional information.

In addition, differently from the case of setting the wide insensitive band in consideration of the variation of the spring, etc. as the conventional art, the CPU 14 can narrow the range of the insensitive band. Consequently, the operator can instruct the bending by the operation through the lever with a fine inclination angle, thereby obtaining the operability with high precision.

The CPU 14 resets the neutral position and the insensitive band by using the positional information every automatic return. Therefore, the bending lever 13 of the joystick 12 can be used within the range of the narrow insensitive band even if the variation of the spring, etc. is wide. In the present embodiment, the operational remote controller for bending the bending portion 5b can use an inexpensive joystick with low precision for the neutral position such that the automatically-returned positions are widely varied, thereby reducing costs.

If the bending lever 13 is within the range of the insensitive band, the CPU 14 does not transmit positional information from the joystick 12 and, thus, the CPU 14 can stop the transmission and the processing circuit. In other words, in the present embodiment, a consumed power during an inoperative time of the joystick 12 can be reduced.

Incidentally, in the above embodiment, after converting the analog signal based on the operation of the joystick into the positional information, the operational remote controller outputs the positional information to the control circuit. However, the function for conversion into the positional information, etc. may be provided at the endoscope control unit. More specifically, the remote control circuit 21 may be provided at the endoscope control unit and the analog signal from the joystick may be transmitted to the remote control circuit. In this case, an apparatus using an existing joystick can be constituted.

Figure 6:
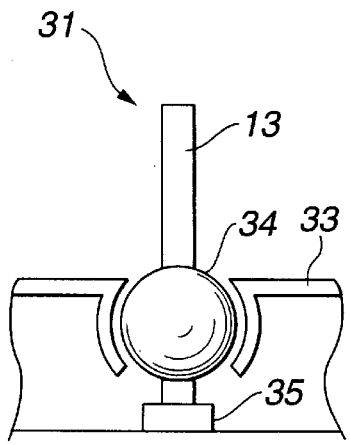
FIG. 6 is an explanatory view schematically showing the constitution of a joystick in an operational remote controller in FIG. 5.
Figure 5:
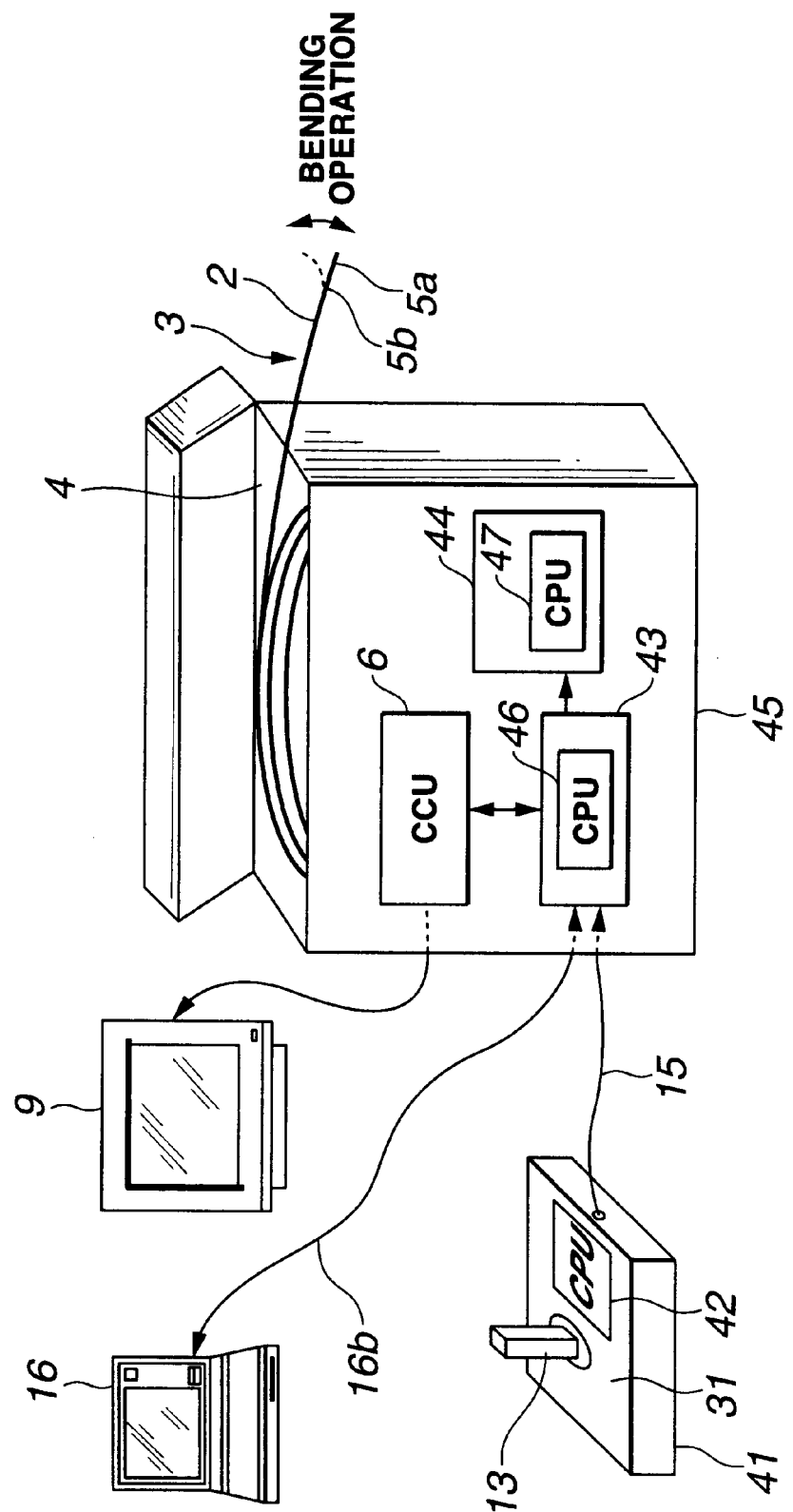
FIG. 5 is an explanatory view showing the overall of an endoscope system including an endoscope apparatus according to a second embodiment.
Figure 7:
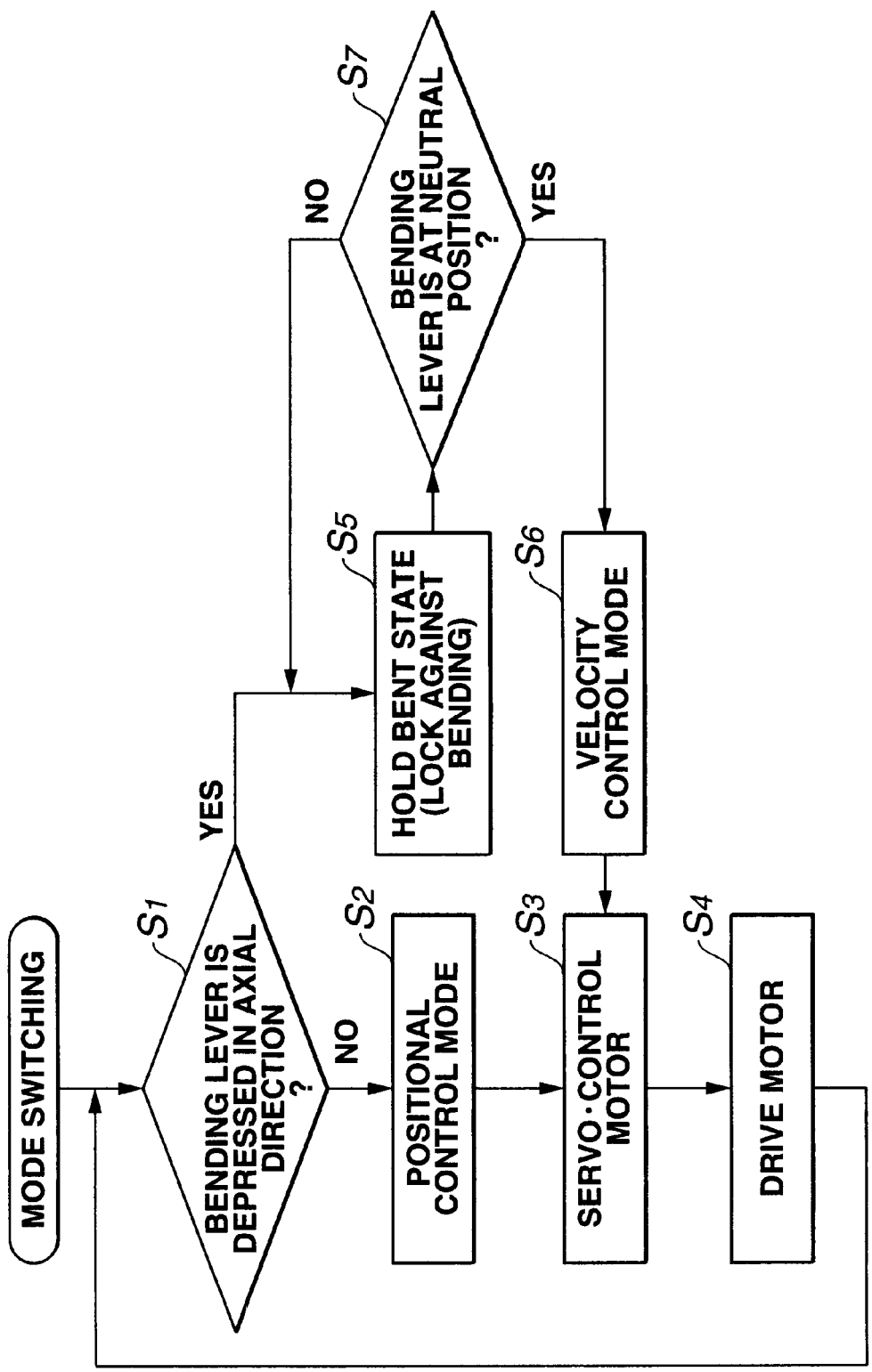
FIG. 7 is a flowchart for explaining operation in FIG. 7.

FIGS. 5 to 7 relate to the second embodiment of the present invention in which FIG. 5 is an explanatory view showing the overall endoscope system including an endoscope apparatus according to the second embodiment; FIG. 6 is an explanatory view schematically showing the constitution of the joystick in an operational remote controller in FIG. 5; and FIG. 7 is a flowchart for explaining operation. Referring to FIG. 5, the same reference numerals as those in FIG. 1 denote the same components in FIG. 1 and the description is omitted.

In the present embodiment, differently from the first embodiment, in place of the endoscope control unit 1, an endoscope control unit 45 is employed and, in place of the operational remote controller 11, an operational remote controller 41 is employed.

The endoscope control unit 45 differs from the endoscope control unit 1 in that a control circuit 43 and a motor drive circuit 44 are employed, in place of the control circuit 7 and the motor drive circuit 8, respectively. Also, the operational remote controller 41 differs from the operational remote controller 11 in that a joystick 31 and a CPU 42 are employed, in place of the joystick 12 and the CPU 14, respectively.

FIG. 6 shows the cross-sectional view of the joystick 31. The bending lever 13 is implanted to a spherical portion 34 rotatable in the up and down and right and left directions and is provided to be exposed from an upper surface 33 of a case of the operational remote controller 41. The joystick 31 comprises: a variable resistor (refer to FIG. 2) in which a resistance changes corresponding to inclination of the bending lever 13 in the right and left direction and a variable resistor in which a resistance changes corresponding to inclination of the bending lever 13 in the up and down direction. The joystick 31 outputs an analog signal with a level corresponding to inclination angles in the up and down and right and left directions of the bending lever 13 to the CPU 42. The bending lever 13 is energized to be automatically returned to a neutral position by a spring, etc. (not shown).

In the present embodiment, a tactile switch 35 is provided at the lower side of the spherical portion 34 in the joystick 31. The spherical portion 34 is not only rotatable in the up and down and right and left directions but also can be moved in an axial direction of the bending lever 13 by lowering the bending lever 13 in the axial direction.

The spherical portion 34 is energized in the upper direction by the spring, etc. (not shown), and is moved in the lower direction along the axis only when the bending lever 13 is lowered, thereby pressing and switching on the tactile switch 35 at the bottom. Only when the spherical portion 34 is lowered, the tactile switch 35 outputs an on-signal to the CPU 42. The spherical portion 34 is energized to be automatically returned to the neutral position by the spring, etc. (not shown).

The CPU 42 outputs the positional information at levels corresponding to the inclination angles in the up and down and right and left directions of the bending lever 13 to the control circuit 43 via the remote controller cable 15, and also outputs the on-signal of the tactile switch 35 to the control circuit 43 as a mode switching signal.

The control circuit 43 can control each section of the endoscope control unit 45, similarly to the control circuit 7 in FIG. 1. The control circuit 43 incorporates a system control microcomputer or CPU 46 for controlling the motor drive circuit 8 to control the bending angle of the bending portion 5b of the inserted portion 2 depending on the inclination angle of the bending lever 13. Further, in the present embodiment, the CPU 46 in the control circuit 43 can execute not only a positional control mode for controlling the bending angle depending on the inclination angle of the bending lever 13 but also a speed control mode for proportioning the inclination angles of the bending lever 13 to rotational speeds of the motors 27 (refer to FIG. 2). Incidentally, the bending direction conforms to the inclining direction of the bending lever 13 in any mode.

In the present embodiment, the CPU 46 in the control circuit 43 switches these modes by a switch signal based on the on-signal of the tactile switch 35. In other words, when the CPU 46 in the control circuit 43 receives the switch signal in the positional control mode and when it is detected based on the positional information that the bending lever 13 is returned to the neutral position after receiving the switch signal, the CPU 46 transmits a switch command from the positional control mode into the speed control mode to the motor drive circuit 44. When the switch signal is received in the speed control mode, the CPU 46 in the control circuit 43 transmits a switch command from the speed control mode into the positional control mode to the motor drive circuit 44.

The motor drive circuit 44 incorporates a motor drive control microcomputer or CPU 47. The motor drive circuit 8 receives the mode switch command from the control circuit 43 in the CPU 47.

When the mode switching command is received, the CPU 47 keeps the last status in the mode and switches a program to thereafter execute the mode after switch.

For example, when the switch command is received in the positional control mode, the CPU 47 keeps a bent state (bending angle) of the bending portion 5b and simultaneously switches an internal program to the speed control mode for proportioning the inclination angle of the bending lever 13 to the rotational speed of the motor 27 thereafter.

On the contrary, when the switch command is received in the speed control mode, the CPU 47 thereafter switches the program to the positional control mode for proportioning the inclination angle of the bending lever 13 to the bending angle of endoscope.

Incidentally, it is considered that, frequently, the bending lever 13 is returned to the center position at the time of switching from the speed control mode to the positional control mode. In this case, the bent state at the time of switching the mode is returned to a straight state in the positional control mode.

If the speed is high when the bent state is returned to the straight state, a mechanical load is increased and a video image is suddenly displayed, thereby making it difficult to grasp an observed position. Therefore, preferably, the return speed to the straight state is relatively slow.

Then, when switching from the speed control mode to the positional control mode, the CPU 47 relatively decreases a rotational speed of the motor 27, and slowly returns the bending state up to the bending angle corresponding to the inclination angle of the bending lever 13 at the time of straight state or mode switching. Incidentally, the bending speed can be arbitrarily selected in this case and is controlled to a proper bending speed and, thereby, durability and usability can be improved.

The CPU 47 controls the speed of the motor 27 in the speed control mode based on a value obtained by integrating the positional information (value) outputted in proportional to the inclination angle of the joystick.

Incidentally, the relationship between the inclination angle of the lever and the bending angle in the positional control mode is not necessarily proportional and the relationship between the inclination angle of the lever and the rotational speed of the motor in the speed control mode is not necessarily proportional. The bending angle and the rotational speed may be increased and decreased by increasing and decreasing the inclination angle of the lever based on, for example, an exponential function or another calculating formation.

Incidentally, a rotational speed $V_m$ and a rotational angle $\theta_m$ of the motor in the speed control mode are expressed by the following formulations (1) and (2).

$$V_m = K(\theta(t) - \theta_0) \quad (1)$$

$$\theta_m = \int_0^t K(\theta(t) - \theta_0) dt \quad (2)$$

where K is constant, t is time when the joystick is inclined, $\theta(t)$ is the inclination angle after time t, and $\theta_0$ is the angle at the neutral position of the joystick.

Next, operation of the embodiment with the above constitution will be described referring to FIG. 7.

Herein, assume that the operator bends the bending portion 5b of the inserted portion 2. Incidentally, assume that at this point, the CPU 46 in the control circuit 43 has set the mode to the positional control mode. The operator inclines the bending lever 13 of the joystick 31 incorporated in the operational remote controller 41, thereby performing the bending operation.

When the operator inclines the bending lever 13, a signal having a level corresponding to the inclination angle is supplied to the CPU 42. The CPU 42 generates the positional information based on the input signal and transmits the generated positional information to the control circuit 43 via the remote controller cable 15.

The CPU 46 in the control circuit 43 controls the motor drive circuit 44 based on the received positional information (step S2). Thus, the CPU 47 in the motor drive circuit 44 servo controls the motor 27 in accordance with the positional information (step S3), and drives the motor at a predetermined speed for inclining the bending portion 5b (step S4).

Herein, assume that the operator reduces the bending speed and, thereby, the bending angle is finely adjusted. In this case, the operator loweres the bending lever 13. As a result of this operation, the tactile switch 35 of the joystick 31 is turned on, and the CPU 42 generates the switch signal. The CPU 46 in the control circuit 43 receives the switch signal.

Thus, the CPU 46 in the control circuit 43 shifts the process from step S1 to step S5, whereupon the CPU 46 makes the motor drive circuit 44 keep the bent state. Further, when the operator returns the bending lever 13 to the neutral position, or the finger is apart from the bending lever and the bending lever is automatically returned to the neutral position, the CPU 46 in the control circuit 43 detects that the bending lever 13 is located at the neutral position based on the positional information (step S7). The CPU 46 outputs a switch command from the positional control mode into the speed control mode to the CPU 47 in the motor drive circuit 44.

The CPU 47 in the motor drive circuit 44 controls driving of the motors 27 by the speed control mode S6 in which the bending speed is controlled in accordance with the bending angle of the bending lever 13. When the operator inclines the bending lever 13 with a relatively small angle, the motor drive circuit 44 servo controls the motor (step S3) and, thereby bending the bending portion 5b at a low speed corresponding to the inclination angle of the bending lever 13 (step S4). Thus, the operator can finely adjust the bending angle of the bending portion 5b.

Next, assume that the operator lowers the bending lever 31 in the axial direction to return the mode to the original positional control mode. Then, the tactile switch 35 is turned on, whereupon the CPU 46 in the control circuit 43 receives the switch signal. The control circuit 43 outputs a switch command from the speed control mode into the positional control mode to the motor drive circuit 44.

The motor drive circuit 44 slowly changes bending angle of the bending portion 5b up to the bending angle corresponding to the inclination angle of the bending lever 13 at the time of outputting the switch command. According to a general using method, it is considered that at the switching time into the positional control mode, the bending lever 13 is located almost at the neutral position by energization of the spring. Therefore, the motor drive circuit 44 slowly returns the bending portion 5b to the straight state.

When the bending angle of the bending portion 5b changes up to the angle corresponding to the inclination angle of the lever 13 at the time of outputting the switch command, the CPU 46 in the control circuit 43 thereafter performs the positional control to bend the bending portion 5b to correspond to the inclined position of the bending lever 13 at a normal speed.

As mentioned above, in the present embodiment, with simple operation, the operator can arbitrarily switch, the positional control method whereby the operator can easily grasp the actual bending angle and the speed control method whereby the fine adjustment is possible and the operator can arbitrarily change the bending speed, thereby using the switched method.

Incidentally, in the second embodiment, the CPU 46 in the control circuit 43 determines that the bending lever returns to the neutral position. After returning the bending lever to the neutral position, the CPU 46 transmits the switch command to the CPU 47 in the motor drive circuit 44. In contrast, the CPU 47 in the motor drive circuit 44 may determine that the bending lever returns to the neutral position. More specifically, in this case, the CPU 46 in the control circuit 43 supplies the switch command and information corresponding to the inclination angle of the bending lever to the CPU 47 in the motor drive circuit 44. After it is detected that the bending lever is returned to the neutral position, the CPU 47 switches the mode.

Figure 8:
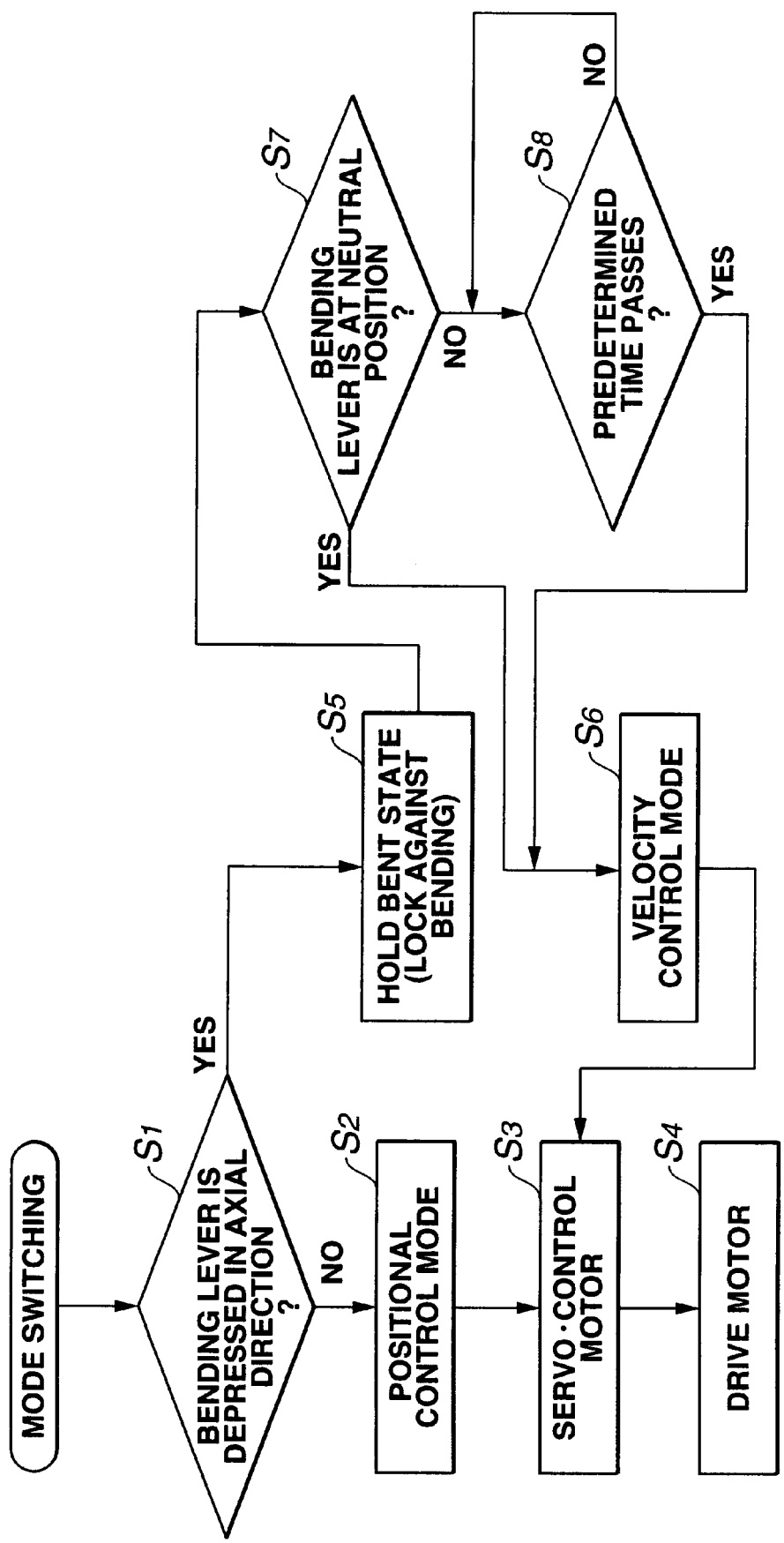
FIG. 8 is a flowchart showing an operational flow used in a third embodiment of the present invention.

FIG. 8 is a flowchart showing operational flow used into the third embodiment of the present invention. Referring to FIG. 8, the same reference numerals as those in FIG. 7 denote the same processing routine in FIG. 7 and the description is omitted.

The configuration of a hardware in the present embodiment is similar to that of the second embodiment.

In the present embodiment, at the time of switching from the positional control mode into the speed control mode, even if the bending lever is not returned to the neutral position, the mode shifts.

The operational flow in FIG. 8 differs from that in FIG. 7 in that step S8 is added whereupon it is determined whether or not a predetermined time passes after lowering the bending lever 13 in the axial direction.

In the present embodiment, with the above-mentioned constitution, after the operator lowers the bending lever 13 in the axial direction, when the bending lever 13 is not returned to the center position after the predetermined time fixed on the program passes, the CPU 46 in the control circuit 43 detects that the predetermined time passes in step S8. Then, the CPU 46 in the control circuit 43 automatically outputs the switch command from the positional control mode into the speed control mode.

Therefore, in the present embodiment, when the bending direction of the bending portion 5b at the time of switching the mode coincides with the bending direction of the bending portion 5b after switching the mode, smooth bending operation becomes possible at the time of switching the control mode.

As mentioned above, in the present embodiment, in the cases of continuously observing one direction, etc., the control modes can be switched smoothly and continuously. Also, the processing routine can be simplified.

Figure 9:
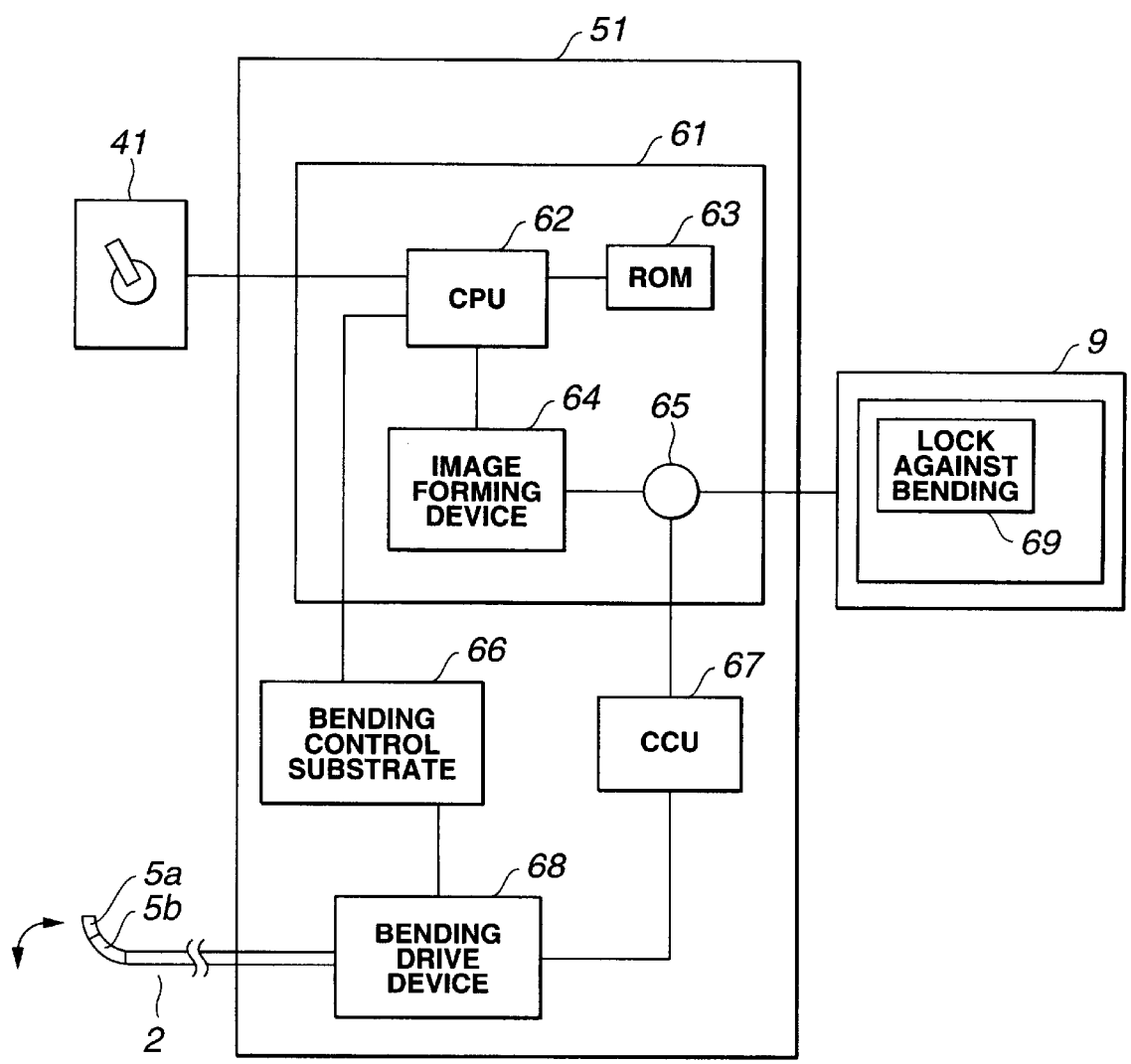
FIG. 9 is a block diagram showing a fourth embodiment of the present invention.

FIG. 9 is a block diagram showing the fourth embodiment of the present invention. Referring to FIG. 9, the same reference numerals as those in FIG. 5 denote the same components in FIG. 5 and the description is omitted. Differently from the second and third embodiments, in the present embodiment, the operator can recognize a locked state of bending.

An endoscope control unit 51 has a constitution almost similar to that of the endoscope control unit 45 in FIG. 5, excluding a point that a display function for indicating the locked stage of bending is added. More specifically, a bending drive device 68 corresponds to the motor 27 and the wires 28 for traction in FIG. 2 and drives the bending of the bending portion 5b of the inserted portion 2. A bending control substrate 66 has a function corresponding to the motor drive circuit 44 in FIG. 5 and controls the bending drive device 68 based on the operation of the operational remote controller 41 while switching the positional control mode and the speed control mode.

A CCU 67 has a constitution similar to that of the CCU 6 in FIG. 5. A system control microcomputer 61 has an equivalent function to that of the control circuit 43 in FIG. 5. The system control microcomputer 61 comprises: the CPU 62; a ROM 63; an image generating device 64; and a superimposing device 65.

The ROM 63 stores therein an operational program of the CPU 62. The CPU 62 has an equivalent function to that of the CPU 46 in the control circuit 43 in FIG. 5. Information indicating that a state shifts to the locked state of bending is supplied in response to the switch command from the bending control substrate 66. The CPU 62 outputs a display command based on the information to the image generating device 64. When inputting the display command accompanied by the locked state of bending, the image generating device 64 generates display data of display (character or graphic) indicating the lock against bending for supplying the generated data to the superimposing device 65.

The superimposing device 65 superimposes the display data from the image generating device 64 to an image formed in the CCU 67 for outputting the superimposed data to the monitor 9.

In the present embodiment, with the above-mentioned constitution, similarly to those in the second and third embodiment, when the operator lowers the bending lever 13 in the operational remote controller 41, the tactile switch (refer to FIG. 6) is turned on whereupon the switch signal is supplied to the CPU 62. When the switch signal is received, the CPU 62 outputs a switch command for switching the mode to the bending control substrate 66.

In association with the switching of the mode, the bending control substrate 66 controls the bending drive device 68, thereby locking the bent state of the bending portion 5b (locking the bending). In the present embodiment, the bending control substrate 66 supplies the information indicating that a state shifts to the locked state of the bending to the CPU 62 in the system control microcomputer 61.

Thus, the CPU 62 outputs the display command to the image generating device 64. The image generating device 64 generates the display data indicating the lock against bending for supplying the generated data to the superimposing device 65. The superimposing device 65 superimposes the display data indicating the locking against bending to the image from the CCU 67 for outputting the superimposed data to the monitor 9.

As mentioned above, a display 69 indicating the lock against bending displays the superimposed image onto a display screen of the monitor 9. When the bending control substrate 66 cancels the lock against the bending, the CPU 62 executes an instruction for stopping an output of the display data on the image generating device 64. Thus, the display 69 indicating the lock against bending is erased from the display screen in the monitor 9.

As described above, in the present embodiment, display indicating the locked state of the bending can be displayed on the monitor and the operator can easily confirm the locked state of the bending. The display indicating the locked state of the bending is superimposed onto the image from the CCU 67. The operator can easily confirm the locked state of the bending without taking his eyes off the endoscope image.

Incidentally, the present embodiment shows an example in which the bending control substrate 66 outputs a signal indicating the completion of locking operation of bending to the CPU 62 and, thereby, the CPU 62 executes the display instruction. However, the completion of locking operation of bending is determined by the system control microcomputer 61 and then the display instruction may be executed.

Figure 10:
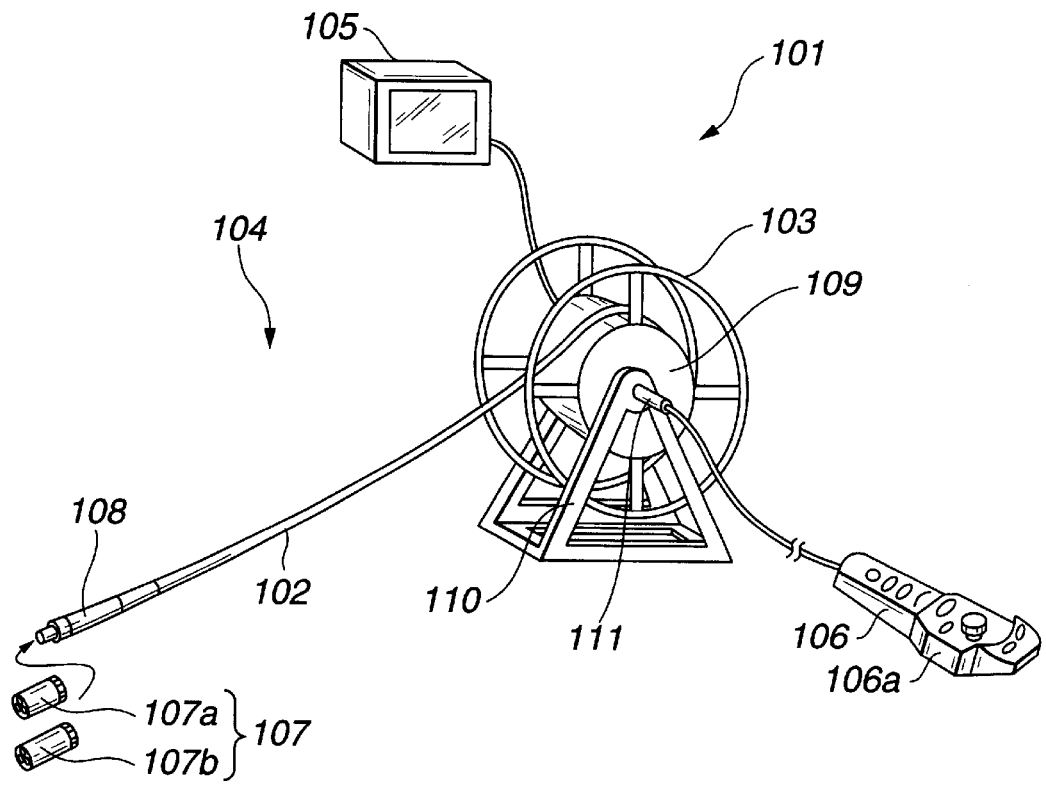
FIG. 10 is a diagram showing the overall constitution of an endoscope apparatus according to a fifth embodiment of the present invention.
Figure 11:
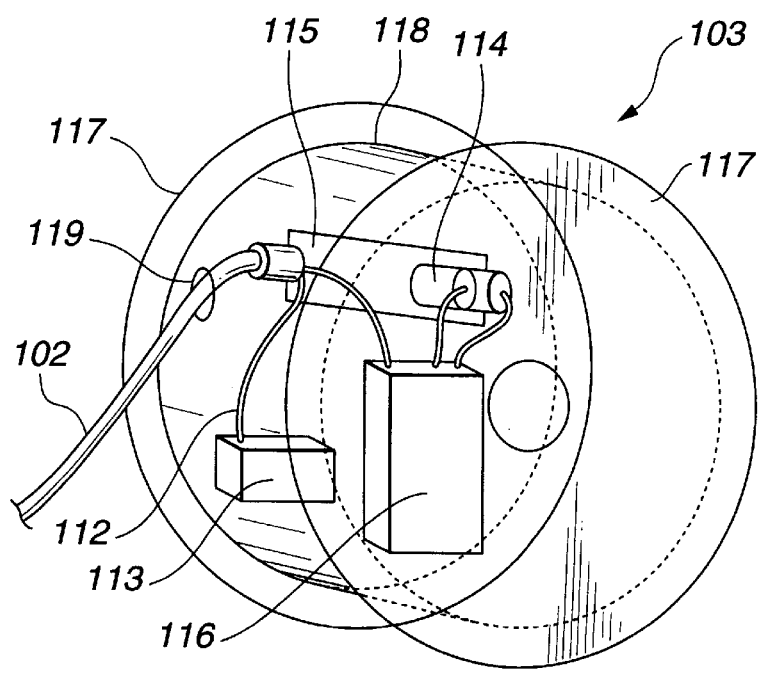
FIG. 11 is an explanatory view of the structure of a drum in FIG. 10.
Figure 12:
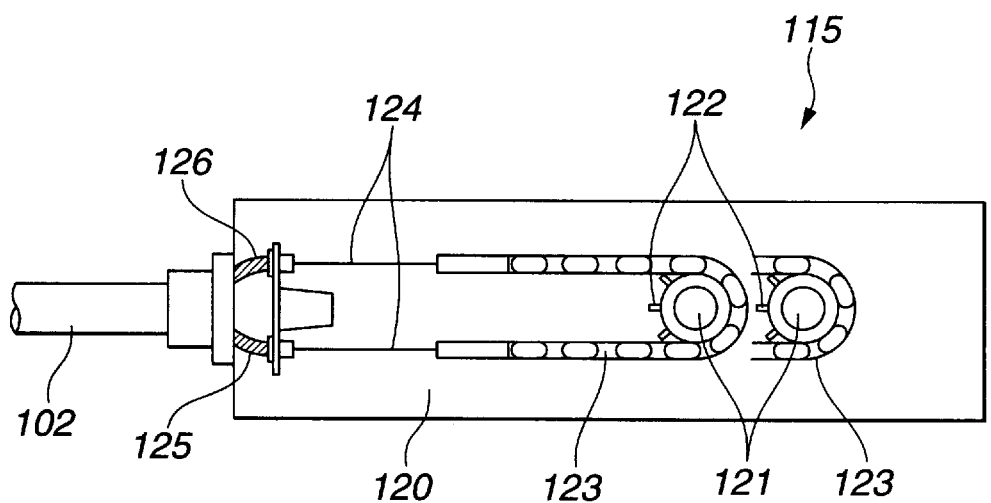
FIG. 12 is an explanatory view showing the structure of a motor drive in FIG. 11.
Figure 13:
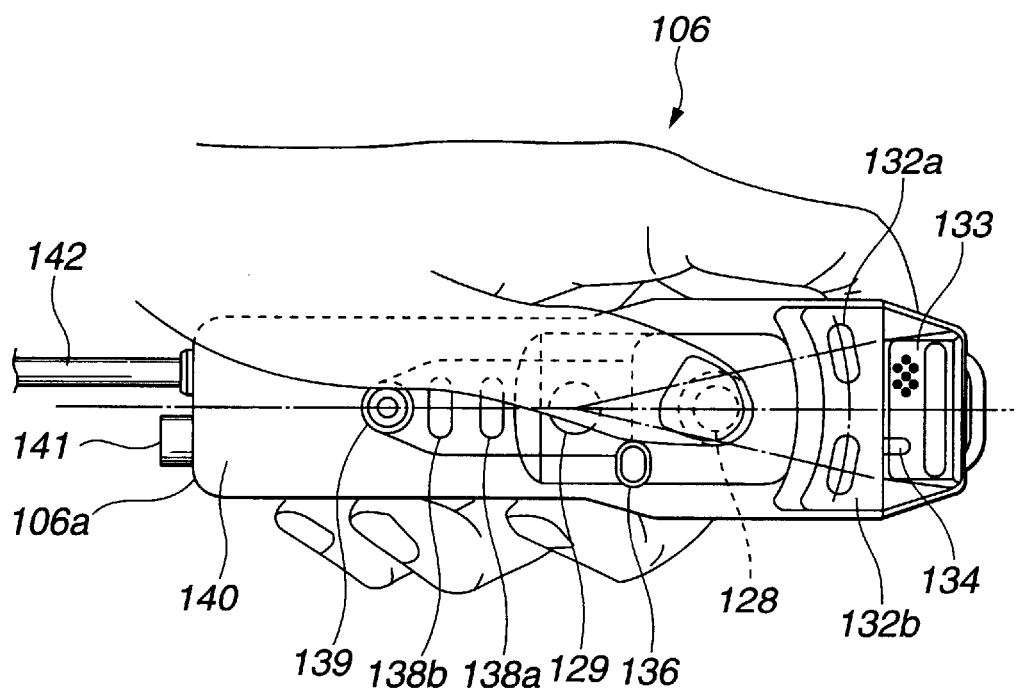
FIG. 13 is a front view showing an operational remote controller according to a fifth embodiment of the present invention.
Figure 14:
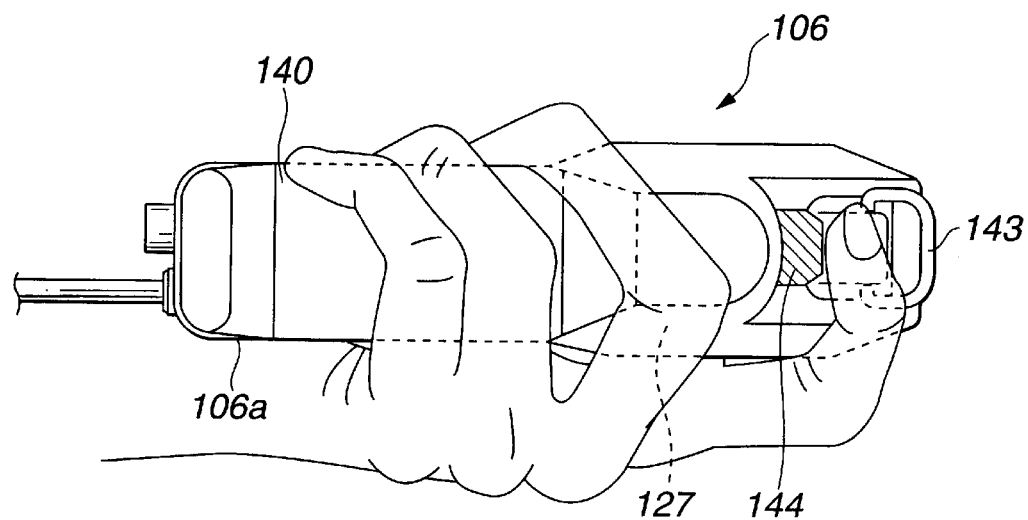
FIG. 14 is a back view showing the operational remote controller.
Figure 15:
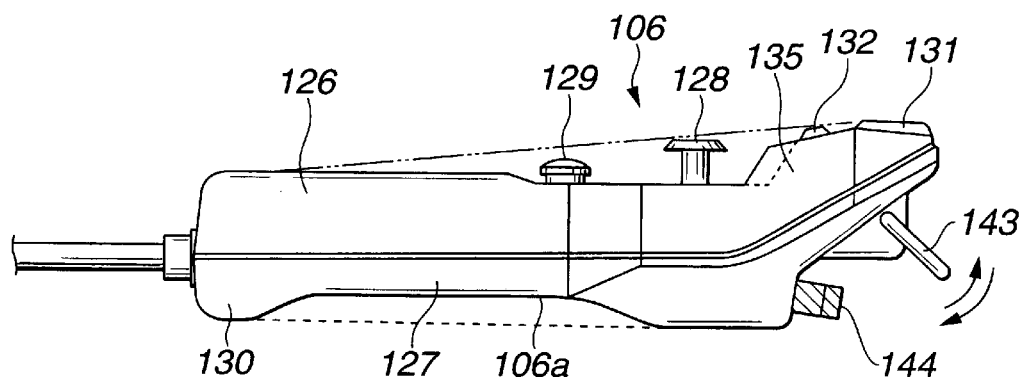
FIG. 15 is a side view showing the operational remote controller.
Figure 16:
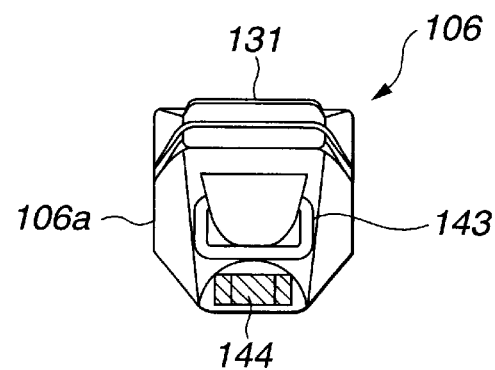
FIG. 16 is an upper end view showing an upper end of the operational remote controller.
Figure 17:
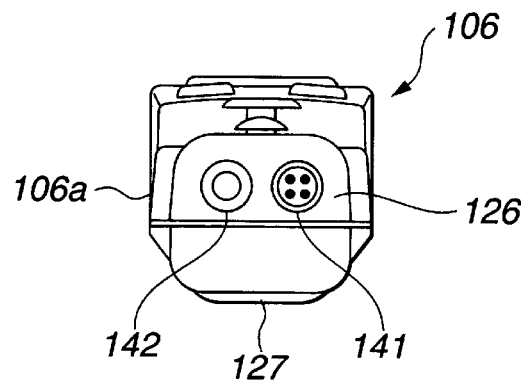
FIG. 17 is a lower end view showing a lower end of the operational remote controller.
Figure 18:
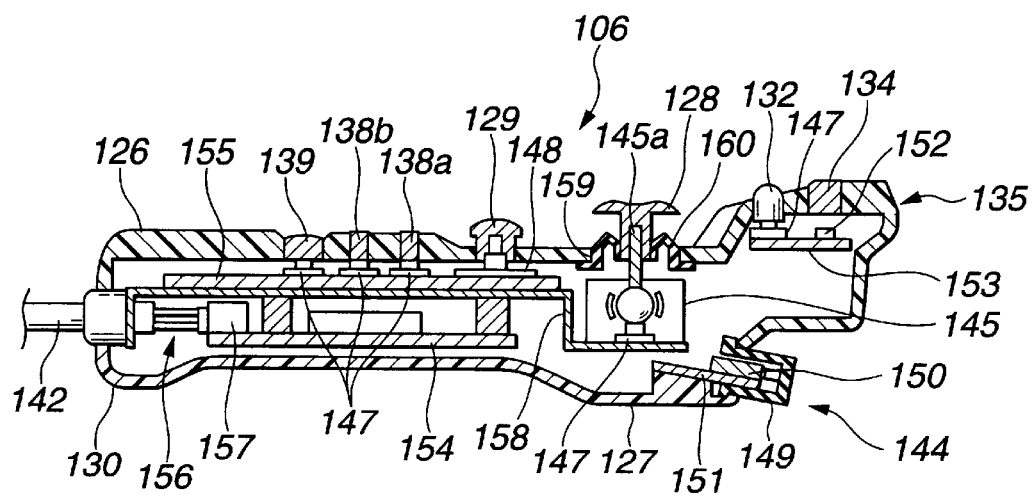
FIG. 18 is a cross-sectional view showing the operational remote controller.
Figure 20:
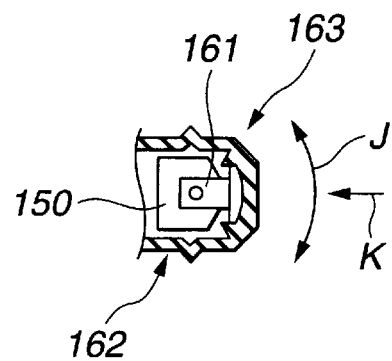
FIG. 20 is a constitutional cross-sectional view showing the constitution of a slide switch of the operational remote controller.
Figure 21:
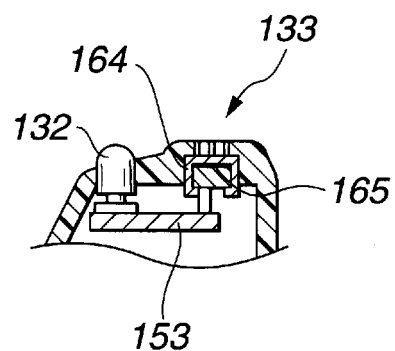
FIG. 21 is an explanatory view showing the structure of a microphone of the operational remote controller.
Figure 22:
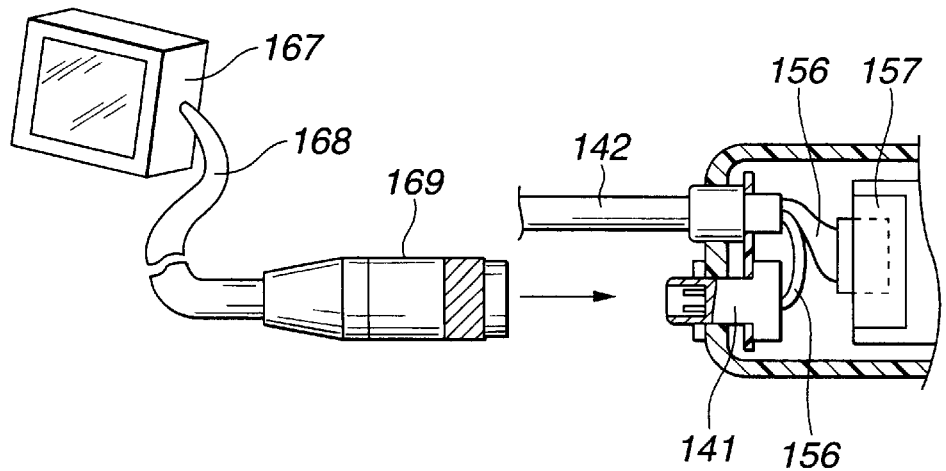
FIG. 22 is an explanatory view showing a relationship between a connector for LCD and a cable in the operational remote controller.
Figure 23:
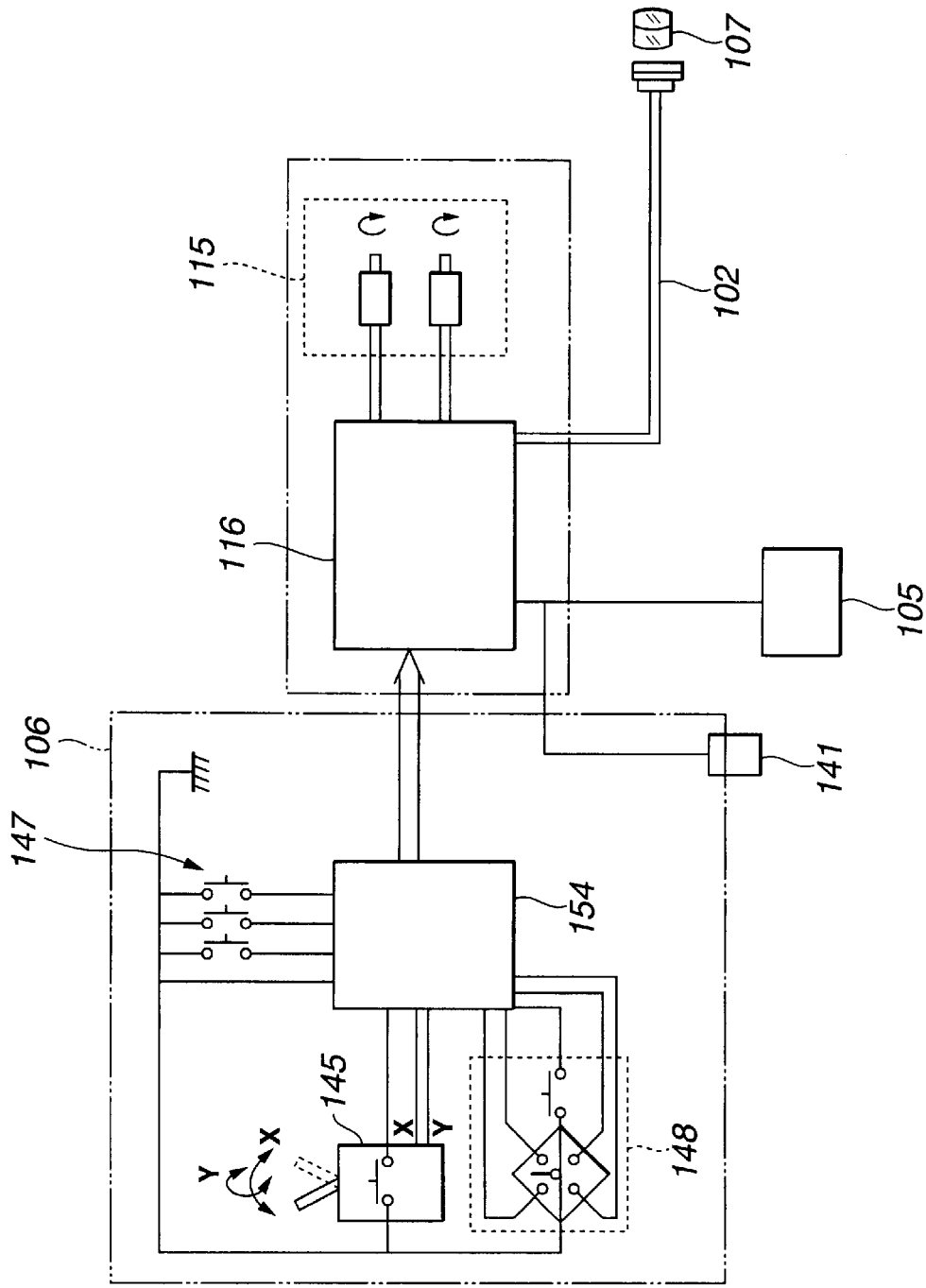
FIG. 23 is a block diagram showing a relationship between the operational remote controller and an endoscope main body.

FIGS. 10 to 23 relate to the fifth embodiment of the present invention in which FIG. 10 is an overall constitution diagram showing the overall constitution of an endoscope apparatus according to the fifth embodiment of the present invention; FIG. 11 is an explanatory view of the structure of a drum in FIG. 10; FIG. 12 is an explanatory view showing the structure of a motor drive in FIG. 11; FIG. 13 is a front view showing an operational remote controller according to the fifth embodiment of the present invention; FIG. 14 is a back view showing the operational remote controller; FIG. 15 is a side view showing the operational remote controller; FIG. 16 is an upper end view showing an upper end of the operational remote controller; FIG. 17 is a lower end view showing a lower end of the operational remote controller; FIG. 18 is a cross-sectional view showing the operational remote controller; FIG. 19 is an explanatory view showing various structures of a bending lever; FIG. 20 is a constitutional cross-sectional view showing the constitution of a slide switch of the operational remote controller; FIG. 21 is an explanatory view showing the structure of a microphone of the operational remote controller; FIG. 22 is an explanatory view showing the relationship between a connector for LCD and a cable in the operational remote controller; and FIG. 23 is a block diagram showing the relationship between the operational remote controller and an endoscope main body.

In the present fifth embodiment, in addition to a joystick almost similar to the joysticks described in the above first to fourth embodiments, an endoscope having an operational remote controller (operational remote controller for endoscope) which is provided with key switches for various operations will be described.

As shown in FIG. 10, an endoscope apparatus 101 according to the present fifth embodiment having an endoscope main body 104 comprising a long inserted portion 102 and a drum unit 103 winding and accommodating the inserted portion 102. A monitor 105 is connected to the drum unit 103 in the endoscope main body 104. Further, an operational remote controller 106 is connected to the drum unit 103 in the endoscope main body 104.

An adapter 107 as an end having image pickup means and illuminating means (both not shown) can be detachably attached to the inserted portion 102. The adapter 107 comprises a plurality of types of an adapter 107a and an adapter 107b capable converting an angle of field of view and a direction of field of view. A bending portion 108 capable of bending is provided at a base-end side of the adapter 107 and can be bent by operation from the endoscope main body 104 side.

The drum unit 103 comprises a drum 109 and a bed 110 which rotatably supports the drum 109 in the axial direction. The inserted portion 102 can be wound to the drum 109. The drum 109 incorporates parts constituting a signal processing unit. The operational remote controller 106 is detachably connected to the drum 109 via a connector 111. The monitor 105 is detachably connected to the drum 109 via the connector 111. The signal processing unit, etc. in the drum 109 supply a video signal and a power to the monitor 105.

Next, the detail of the drum unit 103 will be described referring to FIG. 11.

The drum 109 has therein: a light source device 113 for supplying illumination light to an optical fiber bundle 112, which is illuminating means; and a motor drive unit 115 having two motors 114 for towing a wire to operate the bending portion 108. The drum 109 also incorporates a central substrate 116 having a control function for controlling the motor drive unit 115, a signal processing function for converting an image photographed by the image pickup means into a video signal to generate the video signal and for recording images such as a still image and a live image based on the video signal, and a function for controlling the operations of the respective functions. The monitor 105 are electrically connected to the operational remote controller 106 in the central substrate 116. The base-end side of the inserted portion 102 is fixed to the motor drive unit 115. The inserted portion 102 is extended from an inserted opening. 119 pierced to a cylindrical body 118 sandwiched between two side plates 117 of the drum 109.

Next, the detail of the motor drive unit 115 will be described referring to FIG. 12.

The motor drive unit 115 comprises: a supporting plate 120 for fixing the base-end side of the inserted portion 102 and supporting a motor (not shown); two sprockets 122 fixed to an output shaft 121 of the motor; two chains 123 which is engaged with the sprockets 122 and change rotating movement of the sprockets 122 into advancing and retracting movement; a plurality of wires 124 in which one end of each of which is fixed to the end of the chain 123 and the other end of each of which is fixed to the bending portion 108; and a plurality of coil sheaths 125 for protecting the wires 124.

Incidentally, the plurality of wires 124 are four wires, which are the same as the number of ends of the chains 123.

Next, the detail of the operational remote controller 106 will be described.

As shown in FIGS. 13 to 18, the operational remote controller 106 comprises a case 106a which has a volume capable of being held by an upper cover 126 made of a resin having high crashworthiness and a lower cover 127 made of the same resin. A plurality of switches (which will be described in detail) for remotely operating the endoscope apparatus 101 are placed distributively on the front surface and the back surface of the case 106a.

In the case 106a, a convex portion 130 is formed at the back surface side in the lower end and a stepped portion 135 is formed at the front surface side in the upper end. A projection 131 is formed to the stepped portion 135. The convex portion 130 is provided so that the back surface of the convex portion 130 becomes almost plane as represented by a broken line shown in FIG. 15. Further, the plurality of switches (which will be described in detail) provided at the front surface side of the case 106a are placed in a range shown by a dashed line connecting the projection 131 and the lower end. Thus, even if the front surface side is directed underneath and is placed on a desk, etc., the operational remote controller 106 erroneously does not operate if erroneously pressing the switches and the switches can be protected if the operational remote controller 106 is wrongly fallen. Also, since the upper cover 126 and the lower cover 127 are made of the resin having the high crashworthiness, the operational remote controller 106 is not broken if it is wrongly fallen.

The front surface side of the operational remote controller 106 will be described mainly referring to FIGS. 13, 15, 17, and 18.

In order to enable the use of the operational remote controller 106 by grasping it by either of the right and left hands, on the front surface of the operational remote controller 106, a bending lever 128 of the joystick 145 is placed at a slightly upper side from the center on the front surface, an instructing lever 129 is placed at the center on the front surface, a recording button 138a is placed at the lower side of the instructing lever 129, further, a call button 138b is placed at the lower side of the recording button 138a, and a power source button 139 is placed at the lower side of the call button 138b, each of which is placed on the central axis of the upper cover 126.

Also, on the surface of the operational remote controller 106, a brightness button 132a and menu button 132b are placed at the right and left of the central axis of the upper cover 126 at the upper side of the bending lever 128. The bending lever 128 is placed at a position where it is easily operated by the thumb. Also, each lever and other buttons are placed within a range in which the thumb reaches them.

A center button 136 for operating the bending portion 108 to be straight-shaped is provided near the bending lever 128 on the surface of the upper cover 126. The center button 136 is provided to be slightly concaver than the surface of the upper cover 126 so as not to touch the center button 136 erroneously at the time of operating the bending lever 128.

The brightness button 132a is a button for adjusting the brightness of a photographed image. The menu button 132b is a button for displaying or non-displaying the menu. When the operator lowers the menu button 132b, menus are overlappingly displayed on an observed screen displayed on the monitor 105. Among the menus displayed on the monitor 105, when the operator changes the brightness and enhancement of the image, the observed screen displayed on the monitor 105 corresponding to the changes is changed corresponding to the operation.

The instructing lever 129 can switch menu modes. For example, the operator pushes down in vertical and horizontal directions and, thereby, an item in the menu can be selected. Also, the operator pushes the instructing lever 129 and, thereby, the item in the menu can be determined. Incidentally, the instructing lever 129 functions as a switch for selecting the menus when the menus are displayed. By pushing down in the vertical and horizontal directions or askew direction when the observed image is displayed on the monitor 105, the instructing lever 129 can cause the screen to be panned or tilted (can select a portion where a zoom screen is to be displayed on the monitor 105).

The bending lever 128 is a lever for bending the bending portion 108. When the bending lever 128 is lowered in the axial direction, the bending portion 108 changes to the locked state, thereby switching the mode as mentioned in the first to fourth embodiments.

The recording button 138a is a button for recording a still image or a live image. The operation of the recording button 138a enables an instruction for recording the still image when a freeze screen is displayed on the monitor 105, and also enables an instruction for recording the live image when the observed screen is displayed on the monitor 105.

The call button 138b is a button for instructing a call of a recorded image. The operation of the call button 138b enables a thumbnail image to be displayed. The power source button 139 is a button having a function for turning on/off the overall power source.

On the stepped portion 135 at the upper side of the upper cover 126, a plurality of microphone holes 133 for inputting an audio sound and an indicator 134 for displaying the turn-on the power source are placed.

At the lower side of a held portion 140 in the operational remote controller 106, a connector for LCD 141 which connects external equipment other than the LCD monitor and a soft cable 142 which is connected to a connector 111 connected to the endoscope main body 104 are provided.

The stepped portion 135 is stepped against the held portion 140 with a height to prevent erroneous operation of the brightness button 132a and the menu button 132b at the time of operating the bending lever 128. By arranging the brightness button 132a and the menu button 132b which are frequently used on the stepped portion 135, the usability of the operational remote controller 106 is improved. Also, by arranging the brightness button 132a and the menu button 132b on arc centered the center position of the instructing lever 129, the operational remote controller 106 is easily operated by the holding thumb.

Sequentially, the back surface side of the operational remote controller 106 will be described mainly referring to FIGS. 14, 15, 16, and 18.

The lower cover 127 on the back surface of the operational remote controller 106 is constituted in a shape enabling the holding by either of right and left hands. At the upper side of the lower cover 127, a hanger 143 and a slide switch 144 capable of the holding by either of right or left hand are arranged on the central axis of the lower cover 127.

The hanger 143 is used when the operational remote; controller 106 is hung on a hooked member (not shown). Since the hanger 143 is provided at a balanced place, the operational remote controller 106 is straight hung down without inclination even if it is hung on the hooked member.

The slide switch 144 is a switch for inputting an instruction for adjusting magnification of the observed image, thereby enabling left-inclination operation or right-inclination operation. Operation of the slide switch 144 enables output of an instruction for continuous enlarging or reducing the observed image displayed on the monitor 105. The central substrate 116 displays a slide bar on the observed screen of the monitor 105 in accordance with the instruction from the slide switch 144, thereby displaying a zoom ratio. On the other hand, if no operational instruction is outputted from the slide switch 144, the central substrate 116 does not enable the slide bar to be displayed on the observed screen of the monitor 105.

The overall constitution of the operational remote controller 106 will be described referring to the drawings.

As shown in FIG. 15, the bending lever 128 placed at the front surface side of the case 106a and the slide switch 144 placed at the back surface side of the case 106a are arranged at positions where it is most operable by the thumb and the forefinger, respectively. The bending lever 128 is higher than the instructing lever 129 when viewed from the lower side of the case 106a, and the bending lever 128 is provided at the most operable position.

Further, the upper end of the bending lever 128 differs from that of the instructing lever 129 in shape, as shown in FIGS. 15 and 18. The bending lever 128 is concave-shaped to easily hang the finger. The upper end of the instructing lever 129 is spherical-shaped.

Figure 19A:
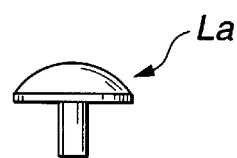
FIG. 19 is explanatory views showing various structures of a bending lever.
Figure 19B:
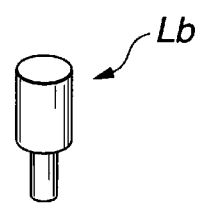
Figure 19C:
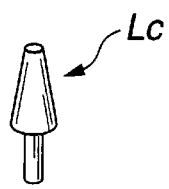
Figure 19D:
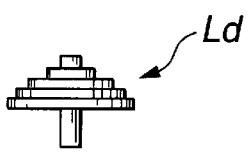

Incidentally, the upper-end shapes of the levers can be varied to match with various operations, for example, a touch portion La is spherical as shown in FIG. 19(a); a touch portion Lb is columnar as shown in FIG. 19(b); a touch portion Lc is cone-shaped as shown in FIG. 19(c); and a touch portion Ld is formed by piling up discs, thus being triangular-shaped with a step when viewed from the side surface as shown in FIG. 19(d).

Figure 24:
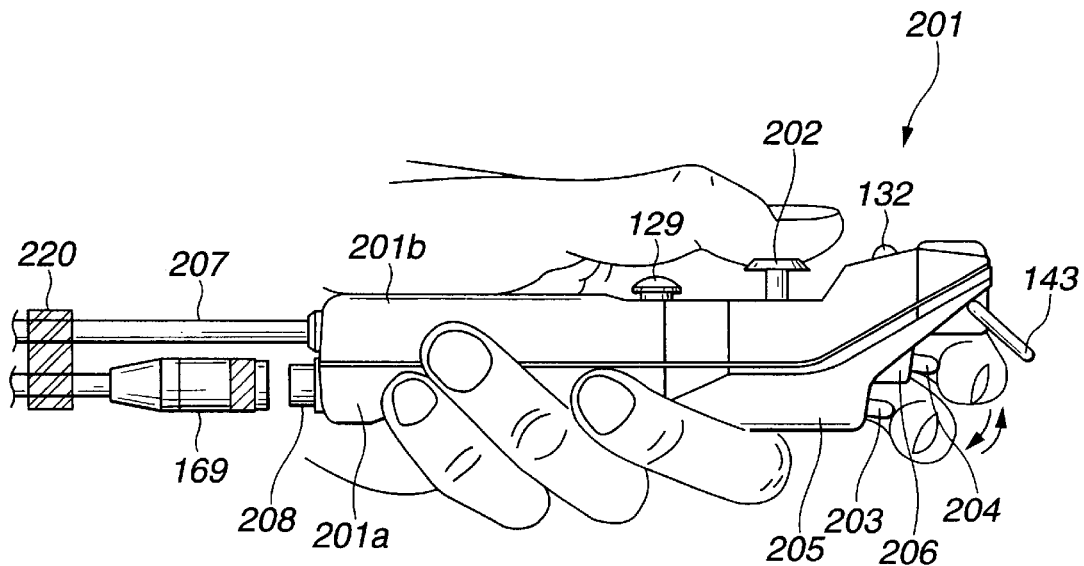
FIG. 24 is a side view showing an operational remote controller according to a sixth embodiment of the present invention.

The connector 141 for LCD and the cable 142 are horizontally aligned as shown in FIG. 17. A cable connected to the connector 141 for LCD (not shown) and the cable 142 are extended in the same direction. Therefore, it is not impeditive for each cable. Of course, as shown in FIG. 24, which will be described hereinafter, when both cables exist, these cables are bound by a binding member 220 and, thereby, it is more user-friendly.

Next, the interior of the operational remote controller 106 will be described mainly referring to FIG. 18.

As mentioned above, the case 106a of the operational remote controller 106 comprises the upper cover 126 and the lower cover 127. The case 106a contains: the menu button 132b; the indicator 134; the recording button 138a; the call button 138b; the power source button 139; the joystick 145; a plurality of tactile switches 147; an instructing switch 148; a lever switch 150; a lever switch substrate 151; an LED 152; an LED substrate 153; a relay substrate 154; a switch substrate 155; a signal line 156; and a connector 157 for substrate. The cable 142 is pull out from the case 106a.

Further, the slide switch 144 comprises a rubber cover 149 made of a soft rubber material and the lever switch 150. The rubber cover 149 has flexibility without interference with the operation of the lever switch 150 and prevents ingress of waterdrop and dust in the case 106a. Further, the lever switch 150 can be inclined at the right and left as shown by an arrow J in FIG. 20, and can be lowered in the axial direction-as shown by an arrow K in FIG. 20, that is, it is a switch capable of outputting signals corresponding to various operations.

As shown in FIG. 20, the lever switch 150 incorporates a lever portion 161. The lever portion 161 is assembled to one part in the rubber cover 149. A buckled portion 162 is provided to the rubber cover 149 to improve the operability.

A switch opening 159 is penetrated in an area to which the bending lever 128 of the upper cover 126 is placed. A rubber boot 160 is placed to the switch opening 159. The rubber boot 160 has flexibility without interference with the bending operation of the bending lever 128 and prevents ingress of waterdrop and dust in the case 106a.

The joystick 145 is an input device for outputting an analog signal corresponding to an angle of the bending lever 128. When the bending lever 128 is lowered in the axial direction, the joystick 145 also outputs an on-signal through the tactile switch 147. More specifically, the joystick 145 is an analog typed joystick by which an output signal is varied corresponding to a slant angle of an operational shaft 145a. When the operational shaft 145a is lowered in the axial direction, the tactile switch 147 for generating a signal is provided to the joystick 145. In place of the analog joystick, a digital joystick comprising an operational shaft and an on/off switch provided corresponding to a direction in which the operational shaft is slanted may be constituted. When the operational shaft has the slant angle, the digital joystick can output the on-signal corresponding to the direction in which the lever is slanted among four directions of X- and Y-directions.

Incidentally, the joystick 145 is automatically returned to the periphery of a predetermined neutral position by an energizing force of a spring, etc. (not shown), similarly to a manner described in the first to fourth embodiments. The control similar to that in the description of the first to fourth embodiments is performed.

When the instructing lever 129 is lowered in the axial direction, the instructing switch 148 outputs another independent on-signal.

By pressing the recording button 138a, the call button 138b, the power source button 139, the menu button 132b, and the brightness button 132a (not shown), the tactile switch 147 of each of the buttons can output the on-signal.

The lever switch 150 is mounted to the lever switch substrate 151. The LED 152 and the tactile switches 147 corresponding to the brightness button 132a and the menu button 132b are mounted to the LED substrate 153. The connector 157 for substrate is mounted to the relay substrate 154. The connector 157 for substrate is connected to the signal line 156 of the cable 142. The respective tactile switches 147 corresponding to the recording button 138a, the call button 138b, and the power source button 139 are placed to the switch substrate 155. The lever switch substrate 151, the LED substrate 153, and the switch substrate 155 are electrically connected to the relay substrate 154 via an FFC cable, etc.

A frame 158 is bent-shaped to attach parts having different heights. The joystick 145, the relay substrate 154, the switch substrate 155, and the cable 142 are attached to the frame 158. The frame 158 is fixed to the upper cover 126, thereby receiving a thrust force at the time of operating the recording button 138a, the call button 138b, the power source button 139, the joystick 145, and the instructing switch 148.

As shown in FIG. 18, the recording button 138a and the call button 138b are arranged on the almost same surface as the front surface of the held portion 140 to prevent erroneous pressing. The power source button 139 is provided slightly lower than the front surface of the held portion 140 to prevent the erroneous pressing as shown in FIG. 18.

A sealing structure that an elastic member to prevent the ingress of the waterdrop and dust is partly pressed is formed at all buttons provided to the surface of the case 106a and the respective openings provided to place the connector 141 for LCD and the cable 142. Similarly, the elastic member is pressed to a seam between the upper cover 126 and the lower cover 127, thereby preventing the ingress of the waterdrop and dust.

The indicator 134 is made of a light-transmittable lacteous resin and has a structure as shown in FIG. 18. The indicator 134 is located at the position opposed to the LED 152. Incidentally, as the LED 152, for example, a green-luminant is used. In the case 106a, the convex portion 130 and the stepped portion 135 form an internal space which functions as a type of bumper. Only the above-mentioned member is arranged in the case 106a and the case 106a has a light weight.

As shown in FIG. 21, the microphone holes 133 are provided for the stepped portion 135 in the case 106a. A microphone 164 is disposed at the position corresponding to the microphone holes 133. The microphone 134 is electrically connected to the LED substrate 153 via a lead wire. In the microphone holes 133, a film 165 for transmitting a sound and preventing the ingress of liquid, dust, etc. is provided at the interior side of the case 106a.

An example in which an LCD monitor 167 is connected via the connector 141 for LCD in the operational remote controller 106 will be described referring to FIG. 22.

The signal line 156 of the cable 142 is connected to the connector 157 for substrate, and a part of the signal line 156 is connected to the connector 141 for LCD. Through the connector 141 for LCD, a power, a vide signal, and an audio signal are supplied from the endoscope main body 104.

The LCD monitor 167 is connected to the endoscope main body 104 by insert-connecting a connector 169 provided for the tip of the cable 168 to the connector 141 for LCD. Thus, the power is supplied to the LCD monitor 167 and also the video signal and the audio signal are supplied, thereby displaying a desired observed image and outputting an audio sound. Incidentally, in place of the LCD monitor 167, a face mounted display FMD (or called an HMD (Head Mounted Display) may be employed.

Next, the relationship among the monitor 105, the operational remote controller 106, and the endoscope main body 104 will be described referring to FIG. 23.

The relay substrate 154 is arranged in the operational remote controller 106. The joystick 145, the tactile switches 147, the instructing switch 148, and other parts are connected to the relay substrate 154. The relay substrate 154 has: an A/D converter; and a CPU to control the joystick 145 similarly to the control in the description in the first to fourth embodiments and for various calculating processes; and an audio amplifier, which are not shown. As shown in FIGS. 11 and 12, the relay substrate 154 is connected to the central substrate 116 provided in the drum 109 via the cable 142.

As shown in FIG. 12, in the drum 109, the central substrate 116 is electrically connected to motors 114 in the motor drive unit 115. The monitor 105 is connected to central substrate 116 via the cable. The connector 141 for LCD is connected to the central substrate 116 via the cable 142. The central substrate 116 receives a signal from the image pickup means at the tip of the inserted portion 102 and signal-processes the received signal to supply a video signal to the monitor 105. The central substrate 116 fetches various instructing signals from the relay substrate 154, then, the motors 114 in the motor drive unit 115 is subjected to control similar to that in the first to fourth embodiments, and the central substrate 116 controls various functions of the endoscope apparatus 101.

Function of the endoscope apparatus 101 and the operational remote controller 106 having the above constitution will be described.

The power source button 139 is pressed, thereby turning on the power source, then, a power is supplied to each portion from the power source (not shown), thereby lighting on the LED 152. The indicator 134 as a pilot lump is green lit on.

After the operator confirms the above operation, he pulls out the inserted portion 102 which winds to the drum 109. The operator photographs an observed target by using the image pickup means provided for the end of the inserted portion while one-hand holding the inserted portion 102 and viewing the front of the observed target by using illuminating means provided for the end of the inserted portion. Then, the image of the observed target is displayed on the monitor 105. In this case, the operator changes from the adapter 107a to the adapter 107b if required, and observes the target by changing a direction of a field of view and an angle of filed of view.

Next, an operating method of each operating means will be described.

(Holding Operation of the Held Portion 140)

As shown in FIGS. 13 and 14, the operator one-handed holds the held portion 140 of the case 106a in the operational remote controller 106. The operator places his thumb of his hand grasping the grasped portion 140 to the bending lever 128 and also places the forefinger of his hand grasping the grasped portion 140 to the slide switch 144.

(Operation of the Bending Lever 128)

The operator keeps the held state of the operational remote controller 106 while observing the monitor 105, and inclines the bending lever 128 in a direction to be observed in the screen displayed on the monitor 105. Then, the joystick 145 is moved corresponding to an amount of operation of the bending lever 128, and outputs a signal indicating the amount of movement in the X- and Y-directions corresponding to the amount of operation. The signal indicating the amount of movement in the X- and Y-directions is changed into a rotational direction control signal of the motors in the relay substrate 154 and is supplied to the central substrate 116. A predetermined amount of power is supplied to the motors 114 of the motor drive unit 115 in the central substrate 154 based on the rotational direction control signal. Thus, the motors 114 rotate and tow the wire 124. The bending portion 108 is bent in the operated direction.

(Operation for Pressing the Bending Lever 128 in the Axial Direction)

When the operator desires the bending to be fixed, he presses the bending lever 128 in the axial direction. Then, a signal is outputted from the tactile switch 147 in the joystick 145 and passes from the relay substrate 154, through the wire 124 and the central substrate 116, whereupon the motor drive unit 115 fixes the bending operation. In this case, when adjusting the bending angle, a function to be operated may be assigned to the tactile switch 147 in the joystick 145. For example, when the bending portion 108 is in a desired bent state and the operator simultaneously assigns a function for fixing the bent state to the tactile switch 147 in the joystick 145, he can operate the bending lever 128 without unhanding the bending lever 128 from his thumb. Also, when the operator assigns a mode switching function to the tactile switch 147 in the joystick 145, in the positional control mode, he can operate for switching the mode from the positional control mode to the speed control mode without unhanding the bending lever 128 from his thumb.

(Operation of the Slide Switch 144)

The operator can operate the slide switch 144 through three operations of left inclination, right inclination, and pressing of the center by using his forefinger while holding the held portion 140 in the operational remote controller 106. Then, a signal is transmitted to the central substrate 116 via the relay substrate 154, similarly to the operation of the bending lever 128. As a consequence, the operator can operate the functions of the endoscope apparatus 101. For example, by pressing the center of the slide switch 144, the operator assigns a function for obtaining a still image to the slide switch 144. Also, by pressing a portion of the left inclination, the operator assigns a function for enlarging the observed image during observation to the slide switch 144. Further, by pressing a portion of the right inclination, the operator assigns a function for reducing the observed image to the slide switch 144. When assigning the functions to the slide switch 144 as mentioned above, fast operation is possible while holding the held portion 140. Therefore, the usability is improved.

(Operation of the Center Button 136)

The operator can operate the center button 136 by moving his thumb while holding the held portion 140 of the case 106a in the operational remote controller 106. The above operation is performed, whereupon the tactile switch 147 operates, thereby supplying a signal to the central substrate 116 from the relay substrate 154. Thus, the central substrate 116 rotates the motors 114 in the motor drive unit 115, then, tows the wire 124, and the bending portion 108 becomes straight. When an image other than the center of the image is displayed, the image in the center of the image is displayed on the monitor 105.

(Operation of the Brightness Button 132a and the Menu Button 132b)

The operator presses the brightness button 132a or menu button 132b by unhanding and moving his thumb from the bending lever 128 while holding the held portion 140 of the case 106a in the operational remote controller 106. When pressing the brightness button 132a, an instructing signal outputted from the tactile switch 147 is inputted to the central substrate 116 via the relay substrate 154. Thus, the central substrate 116 brightens or darkens the video signal. When pressing the menu button 132b, an instructing signal outputted from the tactile switch 147 is inputted to the central substrate 116 via the relay substrate 154. Thus, the menu is displayed on the observed image displayed on the monitor 105. Incidentally, when the menu is displayed, the brightness button 132a may function as a button for returning a layer of the menu to a one-previous menu.

(Operation of the Instructing Lever 129)

The operator performs the following operation by moving only his thumb from the bending lever 128 to the instructing lever 129 while holding the held portion 140 of the case 106a in the operational remote controller 106. First, when the operator inclines the instructing lever 129 vertically and horizontally, the instructing switch 148 operates corresponding to the inclination, thereby outputting the instructing signal corresponding to this operation. The instructing signal generated by the instructing switch 148 is supplied to the central substrate 116 via the relay substrate 154. The central substrate 116 selects an item of the menu based on the instructing signal. By lowering the instructing lever 129 in the axial direction, the instructing switch 148 outputs an on-signal in accordance with this operation. The on-signal is supplied to the central substrate 116 from the relay substrate 154. The central substrate 116 determines the menu by inputting the on-signal.

When a cursor is displayed on the screen of the monitor 105, the cursor may be moved by the signal from the instructing switch 148 which is caused by operation of the instructing lever 129. Also, the operation for pressing the instructing lever 129 in the axial direction may be used as a function of the menu button 132b. Then, operation for all menus can be performed by the single instructing lever 129.

(Operation of the Recording Button 138a and the Call Button 138b)

The operator moves his thumb from the bending lever 128 to the recording button 138a or call button 138b while holding the held portion 140 of the case 106a in the operational remote controller 106. Herein, the operator presses the recording button 138a and, thereby, the corresponding tactile switch 147 operates. Then, an instructing signal outputted from the tactile switch 147 is supplied to the central substrate 116 via the relay substrate 154. When the freeze screen is displayed on the monitor 105, the central substrate 116 allows the still image to be recorded, and when the observed screen is displayed on the monitor 105, the central substrate 116 allows the live image to be recorded.

The operator presses the call button 138b and, thereby, the corresponding tactile switch 147 operates. Then, an instructing signal outputted from the tactile switch 147 is supplied to the central substrate 116 via the relay substrate 154. The central substrate 116 allows the recorded image to be called.

Since the recording button 138a and the call button 138b are located near the instructing lever 129, the usability is improved by assigning an associated function to the instructing lever 129.

Although the specific functions are assigned to the respective levers and respective switches, the present invention is not limited to the above description. Another function may be assigned so as to reduce the number of jobs or errors.

As mentioned above, the following advantages are obtained according the embodiments of the present invention.

(i) According to the embodiments of the present invention, an important switch or lever is placed symmetrically and, therefore, the usability is excellent if using the switch or lever by either of right and left hands.

(ii) According to the embodiments of the present invention, a heavy subject such as a motor is not placed in the case 106a in the operational remote controller 106 and, therefore, the size is reduced and the weight is also reduced.

(iii) According to the embodiments of the present invention, all switches can be operated by the thumb and the forefinger of one hand and, therefore, operation necessary for observation and inspection by the endoscope apparatus 101 is usable.

(iv) According to the embodiments of the present invention, erroneous operation of the buttons is prevented by the positions, the placed state, and the functions and, therefore, erroneous operation is prevented.

(v) According to the embodiments of the present invention, the protecting space is formed by the lower side of the case 106a and the projection 131 and, therefore, breakdown of the levers due to falling, etc. can be avoided.

According to the fifth embodiment of the present invention, although the monitor 105 is formed separately from the operational remote controller 106, the LCD display panel may be mounted to the operational remote controller 106 so long as the purpose is reduction in size and weight.

Figure 25:
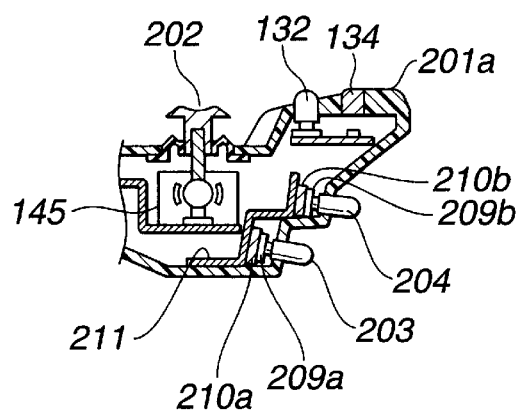
FIG. 25 is a cross-sectional view showing one part of the operational remote controller in FIG. 24.
Figure 26:
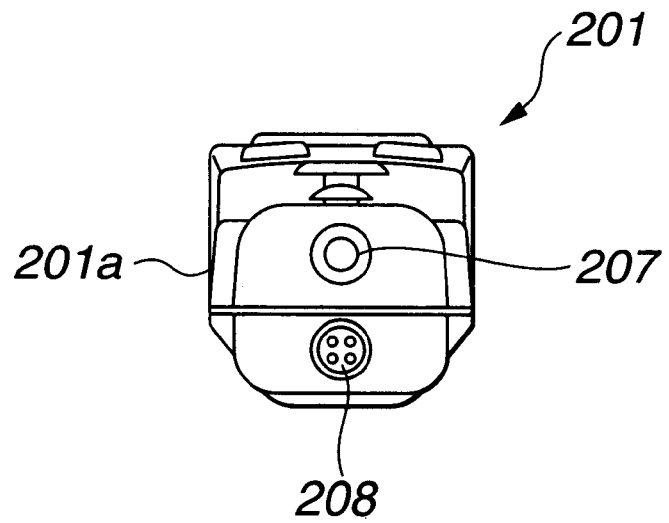
FIG. 26 is a lower end view showing a lower end of the operational remote controller.
Figure 27:
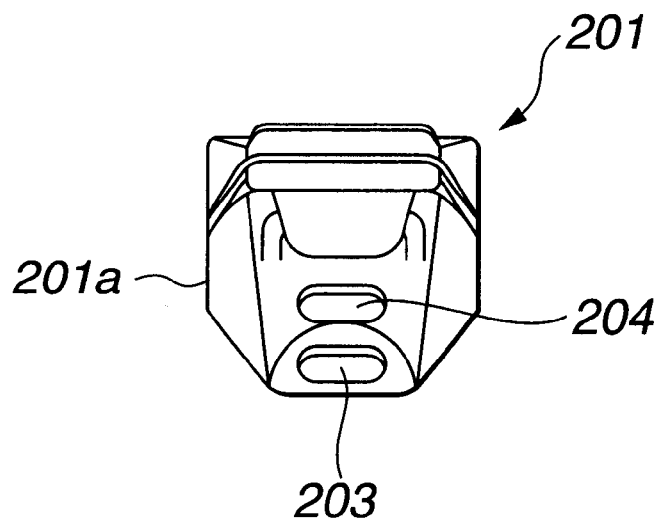
FIG. 27 is an upper end view showing an upper end of the operational remote controller.

FIGS. 24 to 27 relate to the sixth embodiment of the present invention in which FIG. 24 is a side view showing an operational remote controller according to the sixth embodiment of the present invention; FIG. 25 is a cross-sectional view showing one part of the operational remote controller in FIG. 24; FIG. 26 is a lower end view showing a lower end of the operational remote controller; and FIG. 27 is an upper end view showing an upper end of the operational remote controller.

In an operational remote controller 201 according to the present sixth embodiment, a bending lever 202 is similar to that of the fifth embodiment. The operational remote controller 201 differs from that of the fifth embodiment in that two buttons (a freeze button 203 and a recording button 204) are placed in the longitudinal direction at the tip portion side of a lower cover 205 of a case 201a.

More specifically, as shown in FIGS. 24, 25, and 27, the freeze button 203 and the recording button 204 are provided, at different heights, to an uneven portion 206 of the lower cover 205 for the purpose of preventing erroneous operation. As shown in FIG. 25, in the freeze button 203, a tact switch 209b can be operated. The tact switch 209b is mounted to a substrate 210b. The substrates 210a and 210b are supported by a metal subframe 211. The tact switches 209a and 209b are connected to a relay substrate (not shown) via a cable (not shown). The freeze button 203 and the recording button 204 are subjected to a protecting process for preventing the ingress waterdrop and drop in the case 201a, similarly to the above fifth embodiment.

Differently from the slide switch 144 which is adopted in the above fifth embodiment wherein one switch functions as a plurality of functions in the present sixth embodiment. The function is separated the function by the two buttons of the freeze button 203 and the recording button 204 which are independent of each other and the operation is performed by using two fingers. Thereby, probability of erroneous operation is decreased in the present sixth embodiment.

Incidentally, when the operator lowers the freeze button 203, a sill image is displayed on a monitor. When the operator lowers the recording button 204 when a live image is displayed on the monitor, the live image is recorded. When the operator lowers the recording button 204 when the still image is displayed on the monitor, the still image is recorded.

As shown in FIGS. 24 and 26, a cable 207 and a connector 208 for LCD are aligned to the lower end portion of the case 201a in the operational remote controller 201 in the longitudinal direction.

Operation of the aforementioned operational remote controller 201 will be described.

The operator places his thumb to the bending lever 202, his forefinger to the recording button 204, and his middle finger to the freeze button 203, while one-hand holding a held portion of the case 201a in the operational remote controller 201.

The operator controls the bending lever 202 and, thereby, a bending portion of an inserted portion is bent or locked.

Also, the operator presses the freeze button 203, when the operational remote controller 201 is operated while observing the screen of the monitor. Then, the tact switch 209a is operated and outputs a still image instructing signal. This still image instructing signal is supplied to the central substrate via the relay substrate. Consequently, an image displayed on the monitor becomes the still image.

The operator presses the recording button 204, when the operational remote controller 201 is operated while one-hand holding the operational remote controller 201 and observing the monitor. Then, the tact switch 209b is operated and outputs a recording instructing signal. This recording instructing signal is supplied to the central substrate via the relay substrate. Consequently, when the image displayed on the monitor is a still image, the still image is recorded to a recording image recording function. Also, when the image displayed on the monitor is an observed image, the live image is recorded to a live image recording function.

In the operational remote controller 201 according to the present sixth embodiment, the various buttons are placed on the central axis. Therefore, the usability is excellent in the case of using either of the right and left hands.

Also, in the operational remote controller 201 according to the present sixth embodiment, the cable 207 and the connector 208 for LCD are aligned in the longitudinal direction, there is no interference with hand and no obstacle occur even if the operational remote controller 201 is held by using either of right and left hands.

As mentioned above, according to the sixth embodiment of the present invention, in addition to acquisition of the advantages similar to those of the fifth embodiment, the following advantages are obtained.

(i) According to the sixth embodiment of the present invention, the recording button 204 and the freeze button 203 are provided at different heights and can be certainly operated without erroneous operation.

(ii) According to the sixth embodiment of the present invention, the recording button 204 is placed on the central axis and, therefore, the usability is increased even in the case of operation using either of the right and left hand.

(iii) According to the sixth embodiment of the present invention, the connector 208 for LCD and the cable 207 are placed to the lower end portion of the case 201a in the longitudinal direction and, therefore, the respective cable 207 and cable for monitor become no obstacle, thereby improving the usability.

While this invention has been described in detail referring to one preferred embodiment of the invention, it should be understood that the invention is not limited to that precise embodiment. Rather, many modifications and variation will be apparent to those skilled in the art without departing from the scope and sprit of the invention as defined in the appended claims.

What is claimed is:

1. An endoscope apparatus comprising:
   an insertion portion having image pickup means and a bending portion provided at the distal end of the insertion portion;
   a bending drive device having a drive source for bending the bending portion;
   display means for displaying an image picked up by the image pickup means;
   an operating unit for remotely controlling the bending portion;
   a plurality of first operating members provided in a protecting space formed by a lower side and a projection on a front surface of the operating unit; and
   a plurality of second operating members located on a back surface of the operating unit.

2. An endoscope apparatus comprising:
   an insertion portion having image pickup means and a bending portion provided at the distal end of the insertion portion;
   a bending drive device having a drive source for bending the bending portion;
   display means for displaying an image picked up by the image pickup means;
   an operating unit for remotely controlling the bending portion; and
   an operating member located on a flat portion of the front surface of the operating unit which can select from a menu displayed on the display means.

3. An endoscope apparatus according to claim 1, wherein the plurality of first operating members are provided along a longitudinal axial direction of the operating unit.

4. An endoscope apparatus according to claim 1, further comprising a hooked member for holding the operating unit at a predetermined position.

5. An endoscope apparatus according to claim 1, wherein the plurality of first and second operating members are provided within an operable range when the operating the operating unit by grasping.

6. An endoscope apparatus according to claim 1, wherein the plurality of second operating members provided at the back surface of the operating unit includes a switch having a plurality of functions aligned in the longitudinal axial direction of the operation unit.

7. An endoscope apparatus according to claim 1, wherein the plurality of first and second operating members can operate at least one of a slide operation in which an input axis is freely rotatable, and a push operation of the slide operation in an input axial direction.

8. An endoscope apparatus according to claim 1, wherein at least one of the plurality of first operating members provided at the front surface of the operating unit is a joystick.

9. An endoscope apparatus according to claim 1, wherein the plurality of first operating members provided at the front surface of the operating unit are provided within an operable range of a thumb of a hand when operating the operating unit by grasping.

10. An endoscope apparatus according to claim 1, wherein the plurality of second operating members provided at the back surface of the operating unit are provided within an operable range of a forefinger of a hand when operating the operating unit by grasping.

11. An endoscope apparatus according to claim 1, wherein the plurality of second operating members provided at the back surface of the operating unit are switches for generating at least one kind of signals corresponding to an inclined direction of an input axis when the input axis is freely rotated.

12. An endoscope apparatus according to claim 1, wherein the plurality of second operating members provided at the back surface of the operating unit are switches are outputting a signal different from a signal when an input axis is freely rotated by pushing the input axis in an axial direction.

13. An endoscope apparatus according to claim 1, wherein the plurality of second operating members provided at the back surface of the operating unit are switches for outputting a signal to freeze an endoscope image displayed on the display means by pushing an input axis in an axial direction.

14. An endoscope apparatus according to claim 1, wherein the plurality of second operating members are provided at the back surface of the operating unit are switches for outputting a signal to control a magnification of an endoscope image displayed on the display means in accordance with an inclined direction of an input axis when the input axis is freely rotated.

15. An endoscope apparatus according to claim 1, wherein the plurality of second operating members provided at the back surface of the operating unit are switches capable of selectively operating an operation for freezing an endoscope image displayed on the display means by pushing an input axis in an axial direction or an operation for controlling a magnification of the endoscope image displayed on the display means in accordance with an inclined direction of the input axis when the input axis is freely rotated.

16. An endoscope apparatus according to claim 1, wherein at least one of the plurality of first operating members provided at the front surface of the operating unit is an analog joystick for varying an output signal in accordance with a slant angle of an operational shaft.

17. An endoscope apparatus according to claim 16, wherein the analog joystick includes a switch for generating a signal by being connected to the operational shaft to push the operational shaft in an axial direction.

18. An endoscope apparatus according to claim 17, wherein the analog joystick includes a switch which is interlocked to pushing operation of the operational shaft so that a bent shape of the bending portion can be fixed or fixing can be released.

19. An endoscope apparatus comprising:

an insertion portion having image pickup means and a bending portion provided at the distal end of the insertion portion;

a bending drive device having a drive source for bending the bending portion;

display means for displaying an image picked up by the image pickup means;

an operating unit for remotely controlling the bending portion; and a plurality of operating members located on the back surface of the operating unit such that they are within an operable range of a forefinger of a hand when grasping said operating unit.

* * * * *